(12) United States Patent
Brent et al.

(10) Patent No.: US 12,362,065 B2
(45) Date of Patent: Jul. 15, 2025

(54) HEALTH DATA MANAGEMENT AND DISPLAY

(71) Applicant: West Affum Holdings Corp., Grand Cayman (KY)

(72) Inventors: Zoie R. Brent, Kirkland, WA (US); Korine W. Haynes, Woodinville, WA (US); Jonathan P. Niegowski, Issaquah, WA (US); Steven E. Sjoquist, Lynnwood, WA (US); Robert C. Birkner, Snohomish, WA (US); Megan E. Briscoe, Kirkland, WA (US); David P. Finch, Bothell, WA (US)

(73) Assignee: West Affum Holdings DAC, Dublin (IE)

( * ) Notice: Subject to any disclaimer, the term of this patent is extended or adjusted under 35 U.S.C. 154(b) by 201 days.

(21) Appl. No.: 17/950,643

(22) Filed: Sep. 22, 2022

(65) Prior Publication Data
US 2023/0091743 A1   Mar. 23, 2023

Related U.S. Application Data

(60) Provisional application No. 63/247,717, filed on Sep. 23, 2021.

(51) Int. Cl.
*G16H 40/63* (2018.01)
(52) U.S. Cl.
CPC .................. *G16H 40/63* (2018.01)
(58) Field of Classification Search
CPC ........ G16H 40/63; G16H 20/30; G16H 10/20; G16H 15/00; G16H 50/20; G16H 40/67
See application file for complete search history.

(56) References Cited

U.S. PATENT DOCUMENTS

| 3,724,355 A | 4/1973 | Busch et al. |
| 3,724,455 A | 4/1973 | Unger |

(Continued)

FOREIGN PATENT DOCUMENTS

| DE | 102005060985 A2 | 6/2007 |
| EP | 2305110 A1 | 4/2011 |

(Continued)

OTHER PUBLICATIONS

Heartstart MRx and XL AED Algorithm—Application Note, Jul. 2001, Edition 2 Philips Healthcare, USA.

(Continued)

*Primary Examiner* — Chad A Newton
(74) *Attorney, Agent, or Firm* — Lisa Benado; Propel IP Law, PLLC

(57) ABSTRACT

A medical data management system is provided that facilitates expedited review of health data for patient care. The medical data management system includes devices for collecting the health data, associating the health data with health events, optimizing storage of health data, and displaying comprehensive patient data for efficient and rapid review. The system includes a medical monitoring device that uses sensors to acquire health data and logic to specify data blocks of the data that characterize health episodes. Data management device(s) stitch the data blocks according to timelines and store the stitched data blocks as a full episode. The stitched data blocks are rendered for display, as a data presentation with timelines and graphic representations.

21 Claims, 12 Drawing Sheets

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,099,715 B2 | 8/2006 | Korzinov |
| 7,212,850 B2 | 5/2007 | Prystowsky |
| 7,559,902 B2 | 7/2009 | Ting et al. |
| 7,587,237 B2 | 9/2009 | Korzinov |
| 7,753,759 B2 | 7/2010 | Pintor et al. |
| 7,865,238 B2 | 1/2011 | Brink |
| 7,870,761 B2 | 1/2011 | Valentine et al. |
| 7,907,996 B2 | 3/2011 | Prystowsky |
| 7,941,207 B2 | 5/2011 | Korzinov |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,838,235 B2 | 9/2014 | Cowan |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,724,008 B2 | 8/2017 | Sullivan et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,076,656 B2 | 9/2018 | Dar et al. |
| 10,192,387 B2 | 1/2019 | Brinig et al. |
| 10,307,133 B2 | 6/2019 | Kaib |
| 10,449,370 B2 | 10/2019 | Gustavson |
| 10,463,867 B2 | 11/2019 | Kaib et al. |
| 10,589,110 B2 | 3/2020 | Oskin et al. |
| 10,599,814 B2 | 3/2020 | Landrum et al. |
| 11,033,455 B2 * | 6/2021 | Freeman ............. G16H 10/60 |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson et al. |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |

(56) References Cited

U.S. PATENT DOCUMENTS

| | | | |
|---|---|---|---|
| 2018/0184933 A1 | 7/2018 | Sullivan et al. | |
| 2018/0185662 A1 | 7/2018 | Foshee, Jr. et al. | |
| 2018/0243578 A1 | 8/2018 | Volosin | |
| 2018/0361165 A1 | 12/2018 | Jaax et al. | |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0321650 A1 | 10/2019 | Raymond et al. | |
| 2022/0225949 A1 | 7/2022 | Umberger | |
| 2022/0331052 A1* | 10/2022 | Shelton, IV | G16H 30/40 |
| 2023/0049776 A1* | 2/2023 | Freeman | A61B 5/743 |

FOREIGN PATENT DOCUMENTS

| | | | |
|---|---|---|---|
| JP | 2005507747 A | 3/2005 | |
| JP | 2014500099 A | 1/2014 | |
| JP | 2014526282 A2 | 10/2014 | |
| WO | 9839061 A1 | 9/1998 | |
| WO | 2011/146448 A1 | 11/2011 | |
| WO | 2012/064604 A1 | 5/2012 | |
| WO | 2012/151160 A1 | 11/2012 | |
| WO | 2015/056262 A1 | 4/2015 | |
| WO | 2023107404 A2 | 6/2023 | |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

HEALTH DATA MANAGEMENT AND DISPLAY

CROSS REFERENCES TO RELATED APPLICATIONS

This application claims the benefit of the filing date of U.S. Provisional Patent Application No. 63/247,717, filed Sep. 23, 2021, the disclosure of which is hereby incorporated herein by reference for all purposes.

FIELD OF THE INVENTION

The present disclosure generally relates to processing of patient health data for presentation.

BACKGROUND

Various monitoring devices can gather health related data from patients for extended periods of time. For example, a wearable medical device can provide data for a patient wearing the device as the patient goes about day-to-day activities. Such extended wear devices enable clinicians to gain a full picture of specific health aspects of patients.

Large amounts of data can be collected by wearable medical devices. The data need to be quickly sifted through and evaluated to identify potential medical conditions and to initiate proscribed care or treatment.

Medical devices used in cardiac monitoring may have electrocardiogram (ECG) electrodes that detect electrical impulses of the heart when the heart beats. Electricity detected by electrodes is translated into a wavy graph line that is recorded. Certain medical-grade monitoring devices provide critical health information that may require immediate attention, for example, lifesaving alerts of cardiac conditions, and some devices also provide treatment on the fly. Cardiac conditions, as specific examples of health events or clinically significant events, may include ventricular fibrillation (VF), supraventricular tachycardia (SVT), ventricular tachycardia (VT) and other heart related conditions.

SUMMARY

A present medical data management system (also referred to as the "medical system") is provided to facilitate efficient storage of health data and rapid review of the health data, such as clinical review of physiologic data. Episodic data may be acquired prior to, during, and/or after a physiologic event to provide a clinical reviewer with a full picture of the physiologic condition of the patient throughout the event. At the conclusion of the data storage, the entire episode may be made available for transfer to a remote system for clinical review. The medical system may comprise a medical monitoring device and at least one data management device used in processes described herein. The medical data is used for generating a data presentation related to a health event of a patient.

The medical monitoring device includes one or more sensors to acquire data associated with the health event occurring during a period of time. The medical monitoring device also includes one or more hardware processors and logic encoded in one or more non-transitory media for execution by the one or more hardware processors and when executed operable for performing processes. The processes include specifying data blocks of the data that characterize at least one health episode associated with the health event. The processes further include separately storing the data blocks. In some implementations, the processes may additionally include identifying related data blocks, which the medical monitoring device transmits individual data block files collectively as a data group to the at least one data management device.

The data management device(s) are configured for stitching the data blocks according to one or more timelines for storage as a full episode single file. The data management device(s) are further configured for providing the stitched data blocks to be rendered in a data presentation having the one or more timelines and graphic representations of the stitched data blocks for display.

In some implementations, specifying of the respective data blocks may include opening a particular episode of the at least one health episode at a first time and a closing the particular episode at a subsequent second time. In still some implementation, specifying the data blocks may comprise determining that a portion of the data meets a duration threshold and a magnitude threshold to characterize the health episode and that is specific for the health event. The data blocks may include at least two data blocks having at least a portion of overlapping data in a segment of time.

The opening of the particular episode may be, at least in part, in response to the medical monitoring device determining the data meets initiation criteria associated with the health event. The closing of the particular episode may be, at least in part, in response to the medical monitoring device determining the data meets an end criteria associated with the health event.

The data block may include data acquired prior to opening the particular episode and/or after closing the particular episode.

The medical monitoring device is configured for wear by the patient and further comprises a user interface to receive a user trigger. The opening of the particular episode and/or the closing of the particular episode may be, at least in part, in response to the medical monitoring device receiving the user trigger.

In some implementations, the at least one data management device may include an assistant device positioned local to the patient. The assistant device may comprise an interface to request from the medical monitoring device, the data up to a current point in time to define the second time for closing the episode. The assistant device may also include a receiver to receive the data blocks from the medical monitoring device. The assistant may have a transmitter to transfer the data blocks to a remote data management module for stitching the data blocks and providing the data presentation.

The assistant device may receives supplemental information from the patient and the assistant device may transfer the supplemental information to the data management module for integration in the data presentation.

In some implementations, the medical monitoring device may comprise a main unit configured to identify the health event by determining that the data meet at least one event criteria.

The medical monitoring device may include a first data source to acquire a first data type and a second data source to acquire a second data type. Graphical representations of the stitched data blocks of the first data type may be rendered and displayed with regard to a first timeline and graphical representations of the stitched data blocks of the second data type may be rendered and displayed with regard to a second timeline.

In various implementations, a method is provided for managing health data to generate a data presentation related to a health event of a patient, such as implemented by the medical data management system. The method includes acquiring data associated with the health event. Data blocks of the acquired data are specified such that the data blocks characterize at least one health episode associated with the health event. The data blocks may be initially separately recorded. The data blocks are stitched according to one or more timelines to form a full episode that is independently recorded and which is available for access by a reviewed. The stitched data blocks making up the full episode are provided to be rendered in a data presentation. The data presentation is display with the one or more timelines and graphic representations of the stitched data blocks.

According to the method, specifying of the respective data blocks may include opening a particular episode of the at least one health episode at a first time and a closing the particular episode at a subsequent second time. Opening the particular episode may be, at least in part, in response to determining that the data meets initiation criteria associated with the health event, and closing the particular episode may be, at least in part, in response determining that the data meets an end criteria associated with the health event.

The method may also include receiving a user trigger to open the particular episode and/or close the particular episode, where opening and/or closing is, at least in part, in response to receiving the user trigger.

In some implementations, the method further comprises requesting from a wearable medical monitoring device, the data up to a current point in time to define the subsequent second time for closing the episode. The method may include receiving the data blocks from the medical monitoring device, and transferring the data blocks to a remote data management module for stitching the data blocks and providing the data presentation.

The medical data management system may be specialized for generating a data presentation related to a cardiac anomaly event of a patient. Such a medical system may comprise a wearable cardiac monitoring device and at least one data management device.

The wearable cardiac monitoring device may include one or more electrode sensors to acquire electrocardiogram data associated with the cardiac anomaly event of the patient. The wearable cardiac monitoring device may include one or more hardware processors and logic encoded in one or more non-transitory media for execution by the one or more hardware processors and when executed operable for performing certain processes. Such processes may include specifying data blocks of the electrocardiogram data that characterize at least one health episode associated with the cardiac anomaly event, by opening an episode of the at least one health episode at a first time and a closing the episode at a second time. The processes of the logic may also include separately storing the data blocks.

The logic of the wearable cardiac monitoring device may also be for determining that the cardiac anomaly event is a treatable event and the wearable cardiac monitoring device may further include a defibrillator for providing treatment of the cardiac anomaly event.

The at least one data management device may be configured for stitching the data blocks according to one or more timelines for storage as a full episode. The data management device(s) may also be configured for providing the stitched data blocks to be rendered in a data presentation having the one or more timelines and graphic representations of the stitched data blocks for display.

In some implementations, the at least one data management device may include a mobile assistant device positioned local to the patient. The assistant device may comprise an interface to request from the medical monitoring device, the data up to a current point in time to define the second time for closing the episode. The assistant device may also have a user interface to receive symptomatic supplemental information from the patient. A receiver may be included to receive the data blocks from the medical monitoring device. The assistant device may also have a transmitter to transfer the data blocks and supplemental information to a remote data management module for stitching the data blocks and providing the data presentation.

BRIEF DESCRIPTION OF THE DRAWINGS

Various implementations in accordance with the present disclosure will be described with reference to the drawings.

FIGS. 2A, 2B, 2C, and 2D are block diagrams of example data blocks that are stitched data blocks by the medical data management system, in which FIG. 2A shows a data block of an episode, and FIG. 2B shows data blocks of partially overlapping episodes, and FIG. 2C shows data blocks of multiple overlapping episodes, and FIG. 2D shows data blocks of multiple spaced episodes, in accordance with some implementations.

FIGS. 3A, 3B, and 3C are block diagrams of example data blocks initiated by a user and by a wearable monitoring device, and stitched data blocks, in which FIG. 3A shows a data block of a user triggered episode, and FIG. 3B shows data blocks of partially overlapping episodes from different trigger sources, and FIG. 3C shows data blocks of multiple overlapping and spaced episodes from different trigger sources, in accordance with some implementations.

FIGS. 4A, 4B, and 4C are diagrams of the example data presentations displayed on user interfaces, in which FIG. 4A is an example data presentation displaying stitched overlapping data blocks of an VF episode, FIG. 4B is an example data presentation displaying stitched overlapping data blocks of an SVT episode, and FIG. 4C is an example an example data presentation displaying supplemental information associated with a user triggered episode, in accordance with some implementations.

FIGS. 5A, 5B are diagrams of example user interfaces of an assistant device, in which FIG. 5A is an example of a symptoms log screen, and FIG. 5B is an example of a symptoms entry screen, in accordance with some implementations.

DETAILED DESCRIPTION

Figure 1:
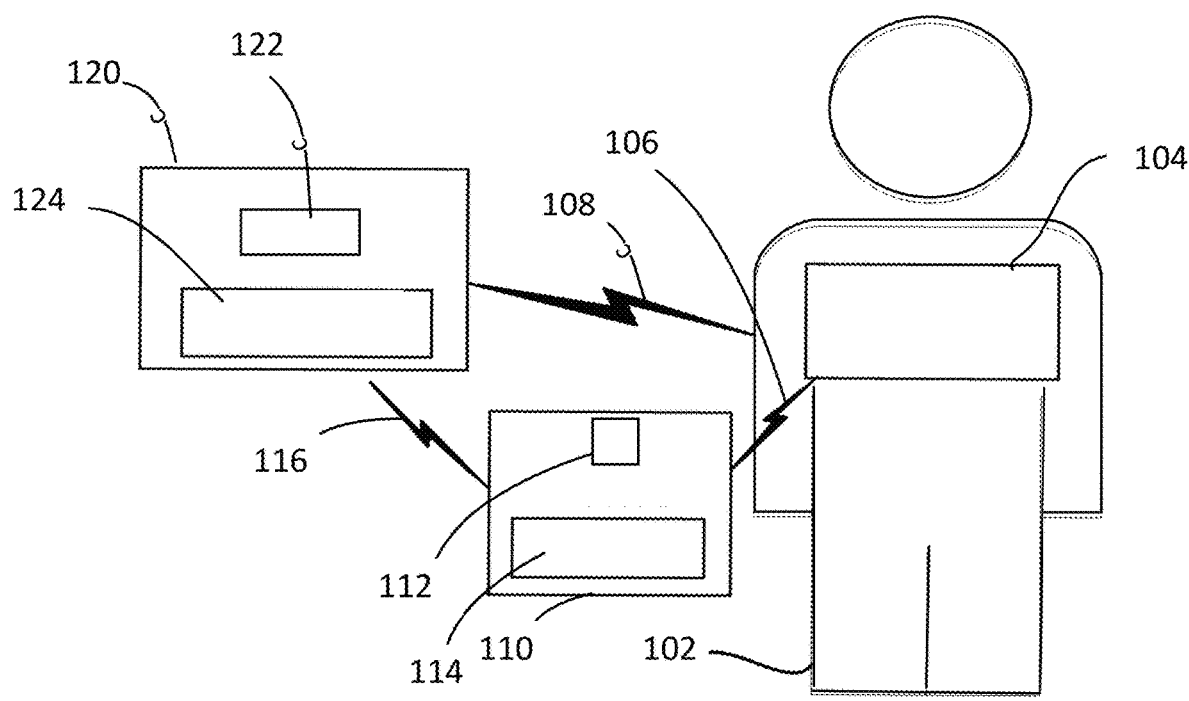
FIG. 1 is a diagram of an example health data management system, in accordance with some implementations.

In the following description, various implementations will be described. For purposes of explanation, specific configurations and details are set forth in order to provide a thorough understanding of the implementations. However, it will also be apparent to one skilled in the art that the implementations may be practiced without the specific details. Well-known features may be omitted or simplified without obscuring the implementations described. The description of the medical data management system provides a framework which can be tailored to individual systems built around the medical data management system. Elements may be described in terms of "basic functionality" or varying degrees of functionality.

The medical data management system (also referred to as medical system) facilitates expedited review of health data for patient care. The medical system includes devices for collecting the health data, associating the health data with clinically significant events (referred to as health events), and optimizing storage of health data. The medical data management system allows for efficient and rapid clinical review of physiologic data by employing several features, including incremental conclusion and packaging of episode data on detection of key events, parallel episode storage during key periods, and "stitching" of episode data together to form a full episode. In addition, the system can be used to combine algorithmically triggered episodic data with patient-triggered episodic data acquired at a same or proximal time. Additional features and combinations of features are possible.

The medical data management system stores data blocks (also referred to as "clips") of episode data that are shorter than the continual data being acquired, that characterize an episode. The data blocks are stored in a manner that maintains a relationship to a single clinically significant health event for example, by a stored event identifier. The data blocks may be available for transfer to a remote device as they are acquired, specified, and stored.

Data blocks are specified based on detection of key happenings, such as patient input, treatment delivery, intrinsic rate recovery, and detection of symptoms characteristic of a health event, such as a specific arrhythmia like asystole or bradycardia. By separating long duration episodes into significant data blocks, more discrete downstream interactions are possible, for example, availability of physiological data to a remote reviewer when deciding to request emergency medical response for a patient.

In some aspects of the medical data management system, data for a long duration episode that covers a single clinically significant health event may be maintained in storage, while also storing shorter data blocks in parallel of the same data. For example, a long duration episode of a shockable arrythmia may be stored to include treatment of the patient. In additional, parallel data blocks for a sub episode prior to the shock delivery, e.g., 15 seconds before, as well as a sub episode after the shock delivery, e.g., 15 seconds after, may be stored. In some implementations, as soon as these parallel episodes are complete, the data blocks may be made available for transfer to the data management device(s) so a remote reviewer is able to follow along during the course of treatment and recovery.

In some implementations, multiple data blocks representing sub episodes may be stitched together to generate a single holistic view of a full episode for a clinically significant event. In some implementations, a field within the data block includes an identifier to associate the data block with one or more additional data blocks and with a particular health event. The medical data management system may collate the data blocks of sub episodes to be stored in a single file and displayed on a timeline for review by a reviewer as a single full episode covering a clinically significant health event.

A health event, as referred to herein, is a confirmed or potential medical condition of a patient. Typically, health events are considered clinically significant and require careful monitoring to determine treatment. Examples of cardiac anomaly events include VF, SVT, VT, etc. Other types of health events are possible.

An episode refers to an occurrence during a period of time in which data or information is acquired. An episode may be defined by an open action and a close action, triggered by a source. Episodes can be triggered from several sensor collecting the same type of data from different locations of the body (for example, ECG from different electrode vectors), different types of data from different types of sensors (for example, ECG from electrodes and spO2 from oximeter, temperature from thermometer), etc. Individually recorded open and close of related episodes may be considered sub episodes to a full episode that form a fuller picture of a health event. Individual episodes may be recorded at a same time, partially overlapping time, or distinct separate times.

A data block refers to a segment or portion of health data that is recorded and originally independently recorded, such as segments of data indicative of an episode data acquired during an episode such as by a sensor of a wearable medical device or manually triggered to record by a user. Data blocks are often variable in length, but in some aspects, may also be uniform in length. The length of a data block may be determined by the system detecting characteristics of a health event from the acquired health data, by manual triggering by a user, regularly scheduled closing of episodes once a predefined time has been reached, or other triggers to close an episode in which the medical monitoring device determines data meets end criteria associated with the at least one health event.

Stitching of data blocks refers to ordering and combining related data along a timeline. Stitching may include portions of overlapping data blocks, parallel recorded data blocks and/or gap periods between data blocks that are void of recorded data blocks. Stitching decisions may be made by the system evaluating data blocks relationship to each other and the health event, or other mechanisms. For example, the system may stitch data blocks that occur with in a specified time ("x" minutes) of each other to be presented as a single view full episode.

For illustration purposes, in an example of a use case of the medical data management system, a medical provider (also referred to as a clinician) evaluates medical data from a representative patient seeking treatment for cardiac episodes that the patient experiences. The medical provider prescribes the representative patient with the medical monitoring system to wear continuously for an extended period of time, such as fourteen or more days, to collect data related to the patient and provide treatment if warranted. In this example, the medical monitoring system includes a wearable device having multiple electrodes that sense heart activity of the patient.

The medical provider in this example, tracks ECG data from two channels of four electrodes. In particular, the medical provider checks for signs of cardiac arrythmias that necessitates treatment. Should a cardiac arrythmia meet criteria for treatment, the medical monitoring system automatically transmits appropriate shock energy to the patient. To gain a fuller picture, the medical provider wants to view such episodes including moments leading up to the shock treatment and after the shock treatment during a recovery period.

The medical provider views a data presentation on a display that shows the data for one channel from periods pre-treatment, during the treatment and post treatment seamlessly on a single timeline with indications of the separate recordings that have been stitched as a single episode, for example points in time that an episode is open and closed. A second timeline similarly shows the data for the second channel.

The medical provider is also interested in how the representative patient experiences symptoms that coincide with the treatable episodes as well, as episodes in which cardiac arrythmias are detected and recorded by the system, but do not rise to the level of a treatable health event. The representative patient is instructed to activate a trigger to record episodes according to symptoms of the patient, such as by pressing a button on the wearable monitoring device. The patient may also input when to end the recording, such as where symptoms subside.

Furthermore, the representative patient in this example is requested to input symptoms into a mobile assistant device of the patient that runs a monitoring application, enables access to a website form, enables logging into a portal, or other data entry mechanisms, to input the symptomatic supplemental information. A simple user interface allows the patient to easily touch or click on a list of symptoms, which is uploaded to the management system for storage and integration into the data presentation according to the time that the symptoms were entered and/or experienced. The medical provider can view all episodes, including stitched overlapping or parallel recordings, whether or not the treatment is applied, as well as the supplemental information of the symptoms according to the timeline of occurrence. With this comprehensive data on the data presentation, the medical provider may make prompt determination of a course of action for the patient.

The medical data management system is not limited to the described use case. As can be recognized by the description herein, there are numerous other situations in which the medical data management system may be employed to stitch and display various types of data for different episodes of a variety of health events.

By comparison to the present medical data management system, other types of medical data systems may separately store and display recorded data, for example as isolated episodes. Such discrete recordings require a reviewer to independently flip between data views of episodes to try to discern relationships of the episodes and manually attempt to compare data from period of time. Such restrictive viewing of data makes it difficult for a user to link the separate episodes in time or achieve a full and prompt picture of a health event experienced by a patient. By contrast, the present data management system provides an inclusive display of data in a data presentation by stitching related recordings according to time and by storing stitched data as a comprehensive episode of a heath event.

The present medical system enables immediate access to data in a manner that is easy to assess in substantially real time while collecting data, with minimal processing delay. Health data is often continuously collected by sensors of the medical monitoring device. The present medical system analyzes the incoming data during acquisition to package significant episodes as data blocks, stitch data blocks and display them potentially at near the time of recording the episode.

The data is recorded in key blocks and arranged according to relationships with other data blocks via a timeline, to avoid the need for a user to attempt to find key data among mounds of recorded data. The display of the data provides a meaningful tool to make quick decisions. Storage of targeted portions of health data can avoid overloading device storage and processing resources that can be heavy for a system that stores all collected data. In some implementations, the medical system allows for overwriting unimportant data and keeping of important data as stitched data blocks.

Other benefits of the health data management system will be apparent from the further description of the system and methods, as described below.

A data management module and/or a display module can be configured to receive data acquired by a medical monitoring device through an intermediary device, such as a mobile assistant device. In some embodiments, the intermediary device (also referred to as "assistant device") can be configured to receive information from the medical monitoring device, and transfer the received information to a remote data management module. In some embodiments, the assistant device can comprise a data management module and/or a display module. The mobile device can be also configured to obtain additional information, which can be objective or subjective about the wearer, for example symptoms, additional wearer feedback, etc.

FIG. 1 shows an overview of an example of the health data management system 100 that employs a medical monitoring device 104 worn by a patient 102 and data management devices. The medical monitoring device 104 collects health data of the patient 102. The data management devices includes an assistant device 110 configured to serve as intermediary device to transfer data to a data management module 122 of a remote computing device 120. The remote computing device 120 further processes the data by stitching and displaying data blocks.

Figure 6:
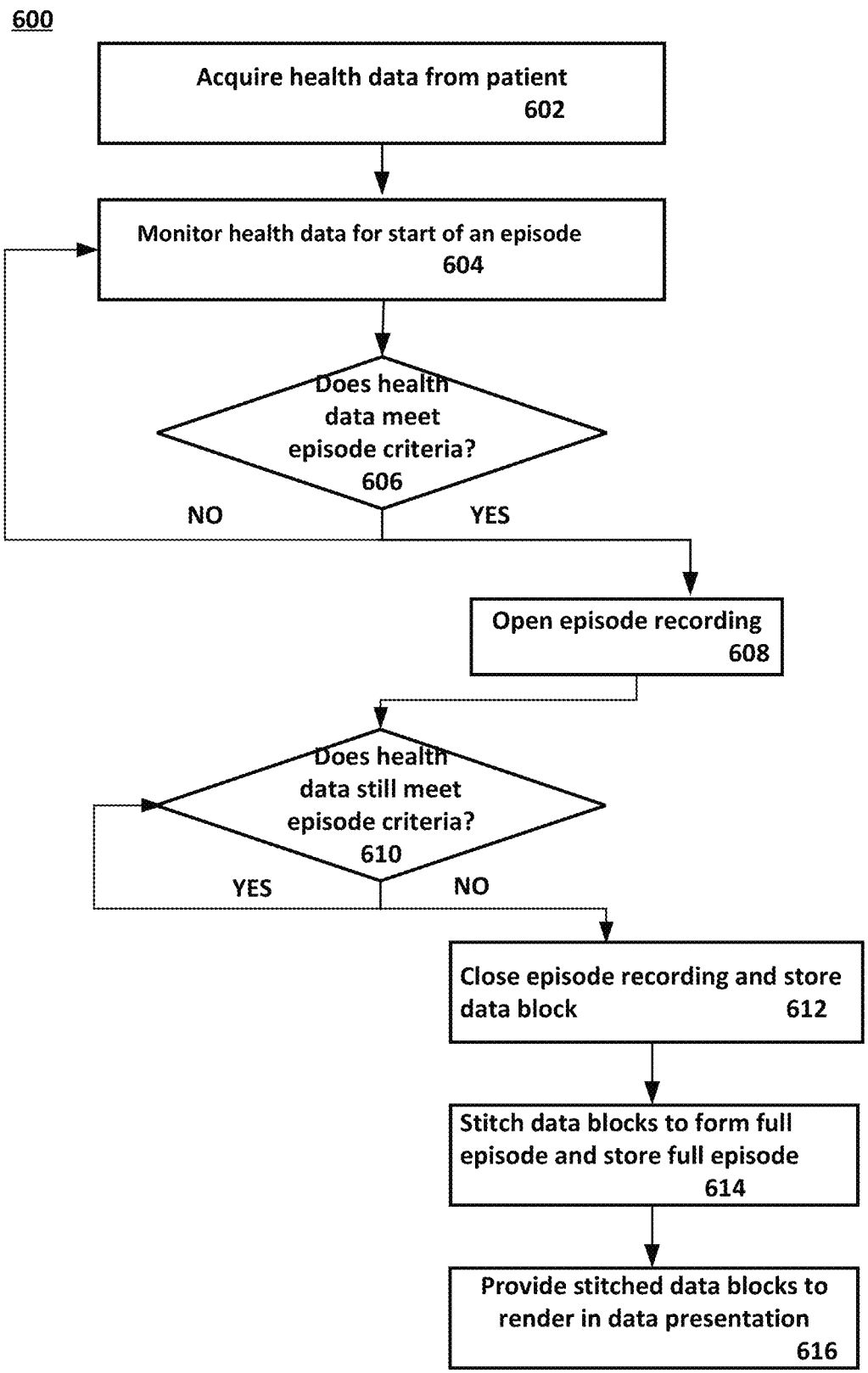
FIG. 6 is a flowchart of an example method for generating a data presentation by stitching data block, in accordance with some implementations.
Figure 7:
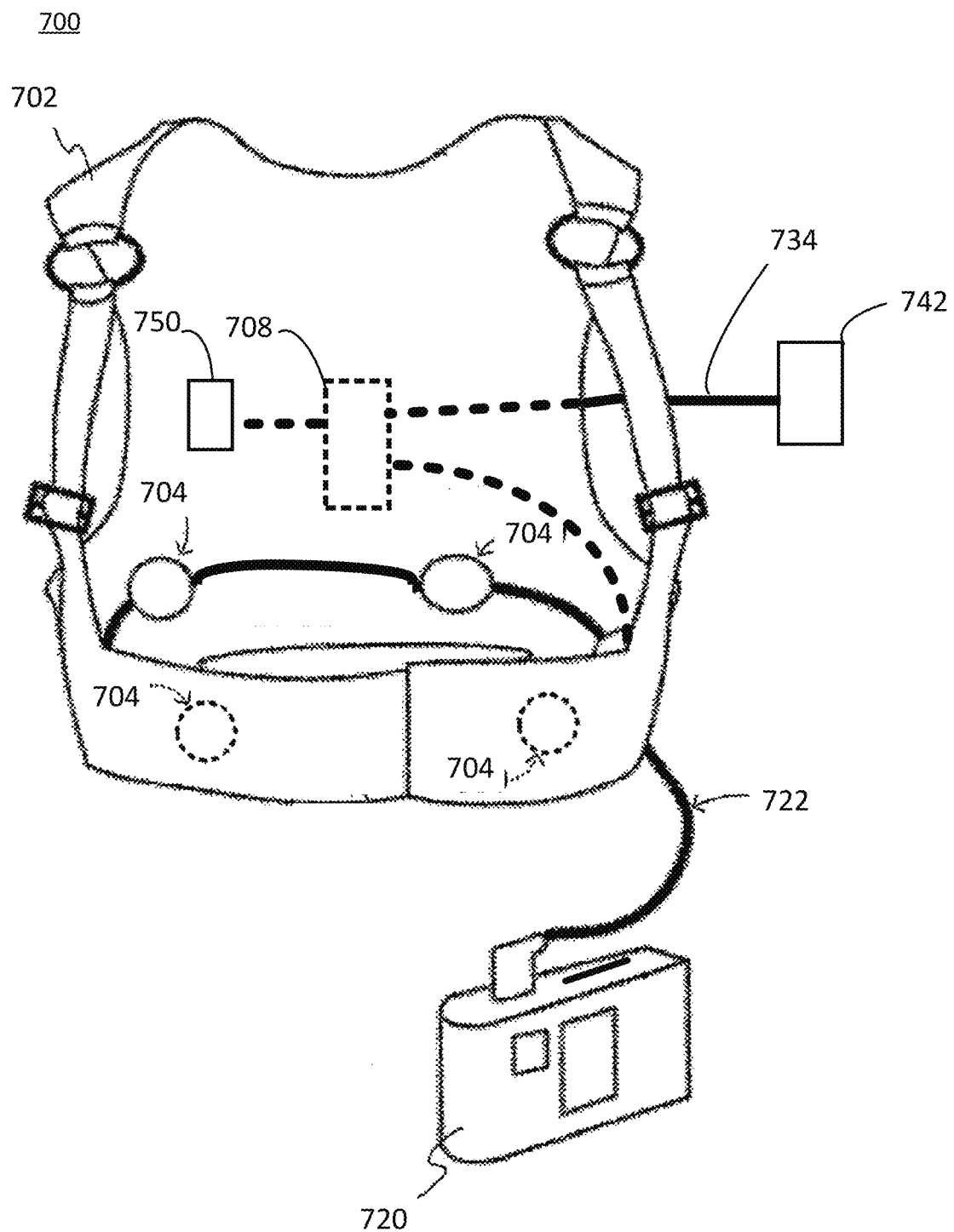
FIG. 7 is a schematic diagram of the example wearable medical monitoring system, in accordance with some implementations.

The medical monitoring device 104 includes one or a plurality of sensors in contact with, or close association to, the patient. The sensors detect parameters of the health of the patient and generate signals reflective of sensed parameters, which is converted into health data by the medical monitoring device 104. Details of an example medical monitoring device 104 are shown in FIGS. 6 and 7 and described below.

In some implementations, the medical monitoring device 104 may be a wearable device (WD) which can be similar to a WD system that also employs defibrillation treatment (e.g., wearable cardiac defibrillator (WCD)), as disclosed in the U.S. Pat. No. 8,838,235, titled: "Wearable Defibrillator System Communicating via Mobile Communication Device," or the U.S. Pat. No. 10,449,370, titled: "Network-accessible data about patient with wearable cardiac defibrillator system," both incorporated herein by reference for all purposes.

The medical monitoring device 104 transfers health data, such as data blocks and/or a health data stream, to one or of the data management devices. For example, assistant device 104 may transfer data blocks and/or a health data stream to assistant device 110 via transfer link 106. The assistant device is typically positioned local to the medical monitoring device 104 and transfer link 106 may employ a number of different near or distance communication technologies.

In some implementations, transfer of data blocks may be pushed on a regularly scheduled basis, such as every 15 minutes. However, transfer of data blocks may also be pulled by request of one or more of the data management devices and may be requested by a user.

At times, the medical monitoring device may assess data blocks to determine relationships between the data blocks, such as a child-parent relationship for example where a first episode is already open and a second episode is opened while the first episode is still recording, the second episode may be considered a child to the first parent episode. In these cases, the medical monitoring device may be configured to hold transferring of one or more data blocks until the completed recording and storage of related data blocks of episodes that are opened and not yet closed. All related data blocks may be transferred as a data group. Data blocks may be marked with a common event to identify a relationship.

In some implementations, a user or the system may override a hold or pause of the transfer of related data blocks, for example, where a data block is long, such as several hours to a day, the system may override a hold and immediately transfer the other related data blocks to the data management system for further processing.

The transfer link 106 may include one or more WANs (Wide-Area Networks) and/or LANs (Local-Area Networks), which may be wired and/or wireless. In some examples, the transfer link 106 may include the Internet and/or one or more cellular networks, among other networks. For example, the transfer link 106 may provide a connection, for example, through a local network to a host computer or to data equipment operated by an Internet Service Provider (ISP). The ISP in turn provides data communication services through the world wide packet data communication network (the "Internet").

The transfer link 106 may operate according to one or more communication protocols, such as Bluetooth™, LTE (Long-Term Evolution), CDMA (Code Division Multiple Access), WiMax (Worldwide Interoperability for Microwave Access), WiFi (Wireless Fidelity), WiFi Direct (Wireless Fidelity Direct), EDGE (Enhanced Data rates for GSM (Global System Mobile) Evolution), 3G (Third Generation), 4G (Fourth Generation), HTTP (Hyper-Text Transfer Protocol), TCP (Transmission Control Protocol), SIP (Session Initiation Protocol), device contact based transfer protocols, device movement based pairing protocols, and other communication protocols.

Although the transfer links 106, 108, 116 are shown as a single networks, it should be understood that the transfer links 106, 108, 116 may include multiple, distinct networks that are themselves communicatively linked. The transfer links 106, 108, 116 could take other forms as well.

In some implementations, the medical monitoring device 104 may instead or also transfer health data, such as data blocks and/or a health data stream, directly to remote computing device 120 via transfer link 108. As the remote computing device 120 may be positioned remote from the medical monitoring device 104, transfer link 108 may employ a variety of communication technologies configured for distant communication, such as described above with regard to transfer link 106. In some implementations, transfer link 106 and transfer link 108 are a same communication network rather than individual transfer links.

The assistant device 110, may be any computing device such as a mobile device, positioned local to the patient or to a person (e.g., local caregiver) in immediate contact with the patient during health data collection, such as a local caregiver in the proximate area of the patient. In some implementations the assistant device 110 may request health data up to a current point in time, such as "up to now" from the medical monitoring device 104 via an interface 112. The request may define a close of an the episode that had been opened, such as by a user trigger, and for which medical data is actively being recorded. In this manner, the assistant device 110 may determine a length of a data block.

In some implementations, the assistant device may append an identifier to a field on particular data blocks to form a relationship between data blocks for collecting and stitching of the related data blocks. The identifier may associate multiple data blocks to a particular health event, according to a particular period of time, or according to other relating criteria.

The assistant interface 112 may also serve as a receiver to receive the data blocks from the medical monitoring device 104. In some implementations, the receiver may be a separate component than the assistant interface 112 that communicates requests with the medical monitoring device 104.

In some implementations, the assistant interface 112 may also transfer the data blocks to the remote data management module 122 for stitching the data blocks and providing the data presentation. The transfer of health data by the assistant device 110 as in intermediary from the medical monitoring device 104 to the data management module, facilitates offloading of power and resource from the medical monitoring device, that otherwise may be consumed by intensive transfer processes. In some implementations, a transfer of data blocks to the remote data management module may be via a transmitter that may be a separate component from the assistant interface 112. In still some implementations a transceiver may transfer data and receive data.

Transfer of data blocks from the assistant device 110 to the remote data management module 122 may be via transfer link 116. The same or similar communication technologies configured for distant data transfer, described above for transfer link 108 may be employed by transfer link 116.

In some implementations, the assistant device 110 may receive supplemental information, such as patient symptoms, that is acquired from other sources, such as input from the patient or local caregiver, rather than from the medical monitoring device 104. For example, the supplemental information is transferred to the data management module 122 for integration into the data presentation. A display of the assistant device 110 rendered information on a user interface via a display module 114. The displayed user interface may be viewed by the patient and/or local caretaker to enter supplemental information into the assistant device 110 via a user interface. Supplemental information may be objective or subjective about the patient, for example symptoms, additional wearer feedback, etc. In some implementations, supplemental information includes information about patient actions, such as wear compliance, steps taken, etc. Details of symptom type supplemental information is described below with regard to FIGS. 5A and 5B.

The data management module 122 can be configured to receive data acquired by the medical monitoring device 104, and to stitch particular data blocks for storage and efficient retrieval to provide a reviewer with a data presentation on a visual display via a display module 124. A reviewer can be a clinical reviewer, a physician, a caregiver, the patient, a researcher, etc. The organized displayed of data in the data presentation can provide the reviewer with information, which can be used in guiding decisions pertaining to the health of the patient, in educating the patient or others regarding health events, research purposes, data analysis for clinical approvals, etc.

The depictions in FIG. 1 is not to be construed as limiting components of the health data management system 100 and how the health data management system 100 is implemented. The health data management system 100 can be implemented in different ways with additional or less devices. For example, in some implementations, the assistant device 110 may include the data management module 122 and the health data management system 100 may not include the remote computing device 120. In other implementations the medical monitoring device 104 transfers data blocks directly to the remote computing device 120 for processing by the data management module 122 and the assistant device 110 is not included in the health data management system 100 for purposes of data transfer.

As shown in FIGS. 2A to 2D, the medical data management system is configured to record select data blocks as segments or portions of a stream of health data captured, such as segments indicative of an episode. Such data blocks can also be referred to as clips of a stream of data acquired by a medical monitoring device. Recording of data blocks includes storing of data blocks in individual files separate from storage of the stream of captured health data.

Figure 2A:
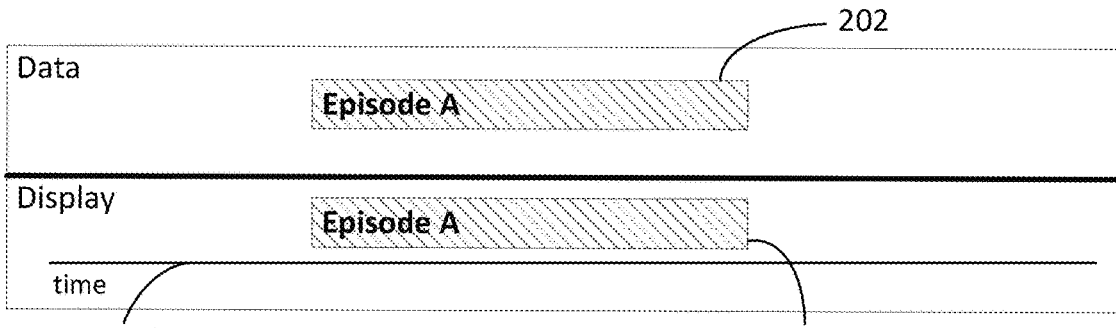

As illustrated in FIG. 2A, a medical monitoring device in the form of a wearable device (WD) detects an episode, Episode A 202. This episode can be a patient-triggered episode, or a WD detected episode. In this example, no other episodes are detected or triggered. A data block for Episode A is stored as an individual file that is not stitched with other data blocks.

The display depicts Episode A 204 in relation to a timeline 206 in a data presentation. In some implementations, the timeline is a time of day during a period of time of data capture, a time segment during which Episode A was captured. In some implementations Episode A is depicted as a graphical representation of the stored data block, such as markings of an opening point and a closing point of Episode A on a graph of the health data stream captured.

Figure 2B:
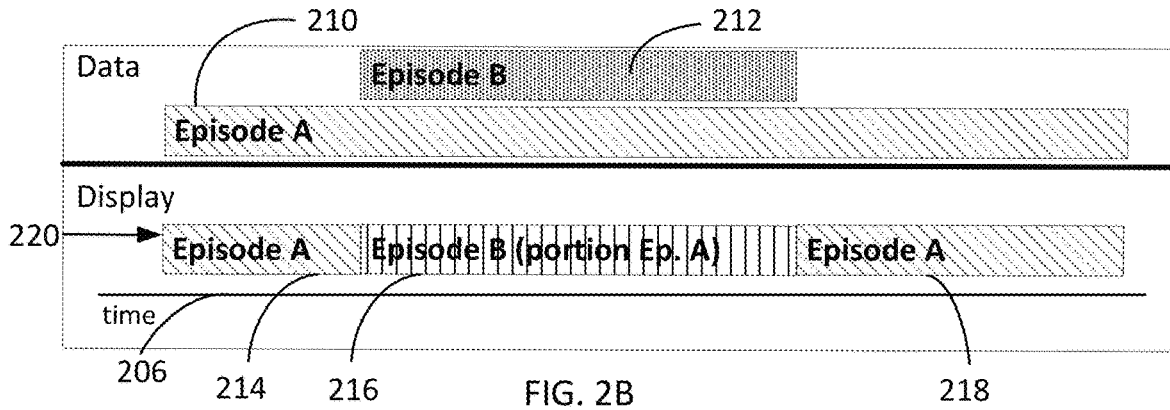

FIG. 2B illustrates a scenario where an episode, Episode A 210, is detected and being tracked, for example, by the WD. Another episode, Episode B 212, is then activated and monitored for period of time. Episode B 212 can be detected by the same detection mechanism as Episode A detection, such as the WD or a different detection mechanism, such as user triggered. Episode B 212 can also be detected from data acquired from the same data source or different data source as Episode A 210.

Episode B 212 monitoring terminates with a close of Episode B 212, but the Episode A 210 monitoring continues. In one scenario, the WD detects and tracks a cardiac arrhythmia (Episode A) before the patient triggers a button and records an episode (Episode B). The recording triggered by the patient ends, but the WD continues to record. An overlapping portion 216 of Episode A and Episode B is stitched with a first portion 214 of Episode A prior to Episode B, in which Episode A and Episode B overlap in a segment of time. A second portion 218 of Episode A lasting after the close of Episode B is stitched to the overlapping portion 216.

The resulting stitched data blocks have the first portion 214, overlapping portion 216 and second portion 218, which are stored as stitched data blocks that may be considered a full episode 220 for review. The original episodes Episode A 210 and Episode B 212 may be considered sub episodes to the newly formed full episode 220. In some implementations, the stitched data blocks are stored as a single file of full episode 220 that may not distinguish the merged sub episodes, Episode A 210 and Episode B 212. In other implementations, the merged sub episodes Episode A 210 and Episode B 212 may be labeled in a manner that enables separation of the stitched data blocks back to the original sub episodes Episode A 210 and Episode B 212, such as upon reviewer request.

In some implementations, the full episode 220 of stitched data blocks may be displayed in response to a reviewer requesting a data presentation showing the full episode 220. For example, a log or listing of episodes may include full episode 220 rather than listing each individual Episode A 210 and Episode B 212. The reviewer may select the full episode 220 from the list to cause display of the full episode 220 having multiple sub episodes noted along a timeline. Other mechanisms to request display of full episode 220 are possible, such as the reviewer inputting a search request for full episode 220 by search terms, an identifier linked to full episode 220, a requesting all full episodes within a particular time period, etc.

In some implementations, multiple events may be connected by various link factors, such as symptomatic, cause/effect, time, e.g., at least partially overlap in time, occur back to back, or occur during a period of time, etc. A reviewer may benefit from viewing episodes that represent connected events on a single data presentation. For illustration purposes, the medical monitoring device may detect a heart arrhythmia and open an episode. Afterwards, the patient may recognize symptoms of feeling unwell, such as shortness of breath, chest discomfort, and nausea. The feeling unwell may be tied symptomatically to the arrythmia event. The events occur at similar or same times. For example, in FIG. 2B Episode A 210 may be a device detected arrhythmia and Episode B 212 may be an event that a patient feels unwell. Episode B 212 overlaps with Episode A 210 in time at overlapping portion 216.

In other situations, a first event may be cause/effect connected to a second event. For example, a diabetic emergency may be detected by a blood glucose monitor and a second arrythmia event may later be detected by ECG's, where recorded episodes occur at non-overlapping times. Each event may have one or more respective episodes that open and close for recording. The event episodes are both viewable on a same data representation, for example on separate timelines and where a viewer may scroll from one time for a first event and another time for a second event. Data blocks for non-overlapping episodes may be stitched with gap periods linking the episodes that occur at different times.

Figure 2C:
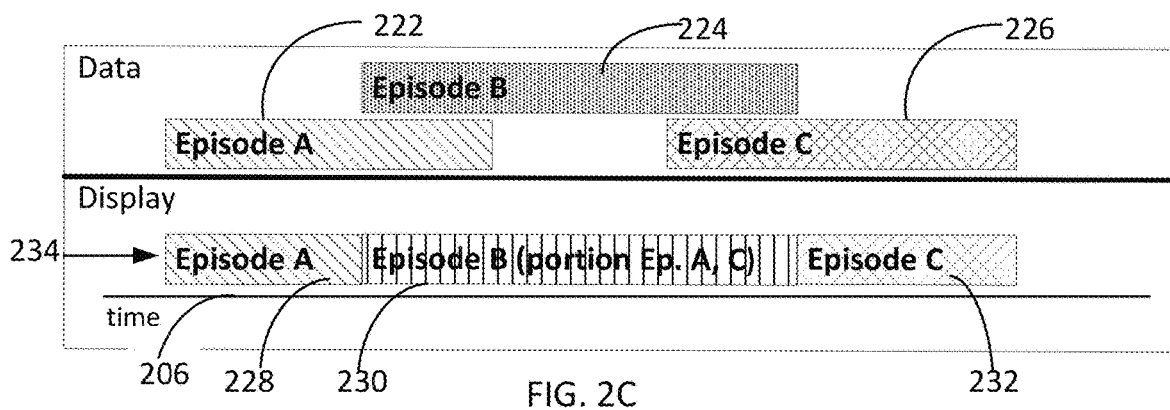

FIG. 2C illustrates a scenario where an Episode A 222 is detected and monitored. Episode A 222 terminates after an Episode B 224 is triggered. Episode B 224 closes after Episode C 226 is opened such that Episode C 226 has an onset before Episode B 224 ends and lasts longer than Episode B.

The stitched data blocks shown on the display as a full episode 234, which includes a first portion of Episode A 228. The stitched data blocks on the display also shows an overlap segment 230 that includes an overlapping portion of Episode A and Episode B as well as overlapping portion of Episode B and C. The stitched data blocks on the display further shows the remainder portion of Episode C 232.

Figure 2D:
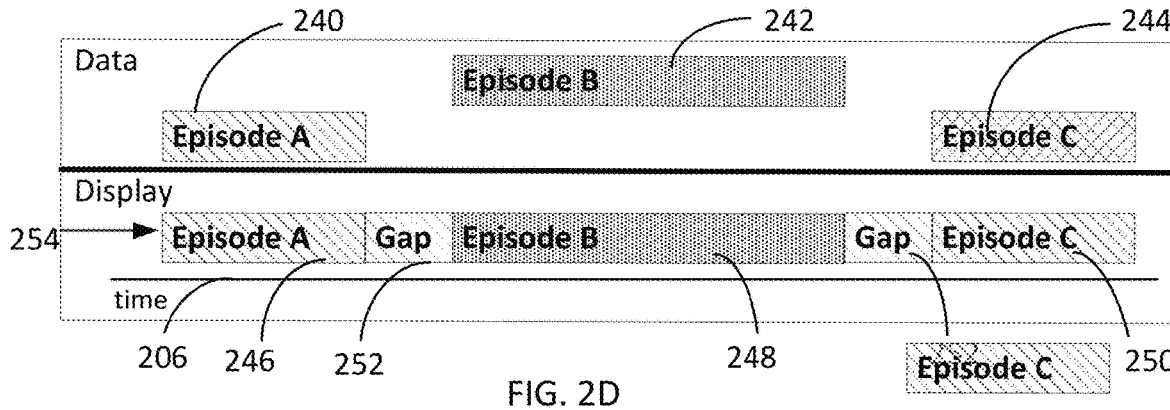

FIG. 2D illustrates a case where an Episode A 240 is detected and terminated. After a period of time after Episode A, a separate Episode B 242 is triggered. Episode B 242 is recorded. There is a period of time after Episode B 242 is recorded and then Episode C 244 is recorded.

The data blocks are stitched with gap periods between the closing and opening of sub episodes to form a full episode 254. Episode A 246 and Episode B 248 are stitched with a gap period 252 during which no episode data is recorded in the full episode. Episode B 248 and Episode C 250 are stitched with gap 252.

Figure 3A:
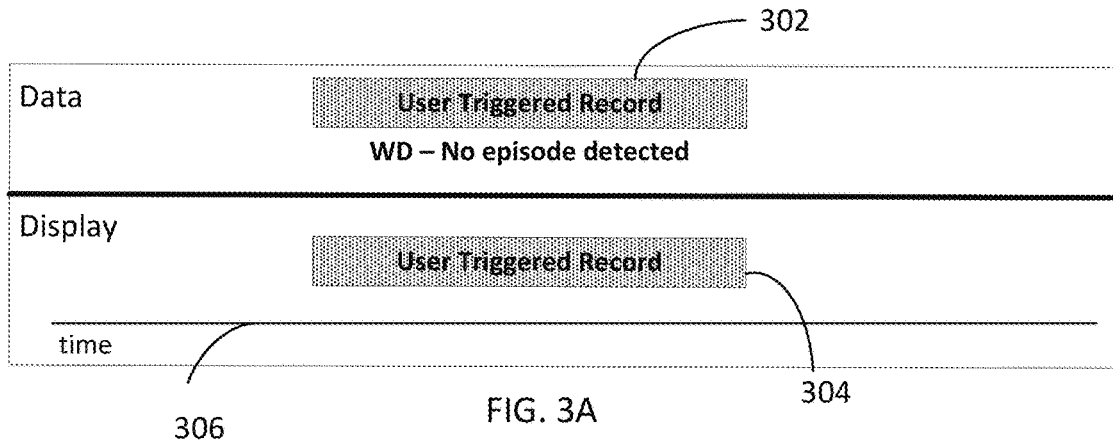
Figure 3B:
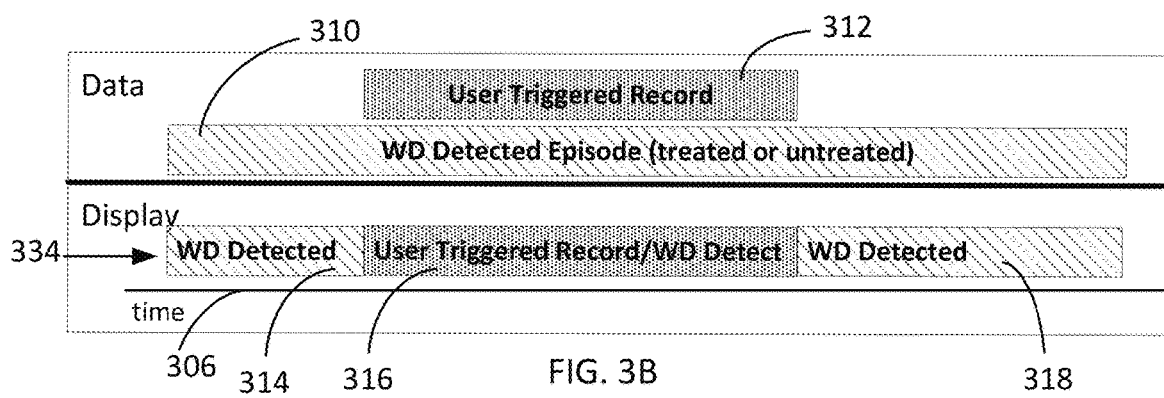
Figure 3C:
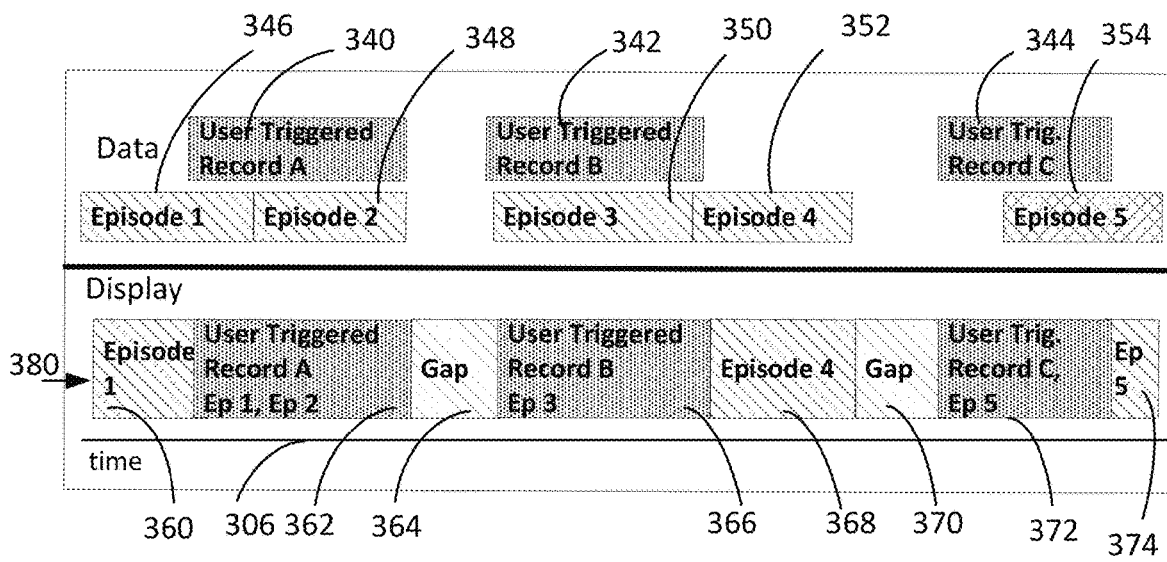

FIGS. 3A, 3B, and 3C depict examples of recording sessions in which initiation of recording of data blocks is by various trigger sources, such as user triggered and wearable monitoring device (WD) triggered recordings for storage and display.

As shown in FIG. 3A, a user triggered recording 302 is initiated by a patient wearing a WD, such as a wearable cardioverter defibrillator. The WD does not detect an ECG anomaly in analyzing the captured ECG health data, but the patient may sense symptoms, or may want to device to record an ECG even though the patient is asymptomatic. The patient can trigger the WD to record the ECG by pushing a button on the wearable device. The WD responds by recording an ECG for a period of time, which is treated as a user or patient triggered episode 302.

The display shows the user triggered recording 304 on a data presentation in relation to a timeline 306. The data presentation may also include information indicative that the WD did not detect an episode and that is no parallel or overlapping episode occurred.

In a further example, a patient or a user, for example a clinician or medical caregiver, may prompt the WD to record an electrocardiogram over a time period and the medical data management system may prompt the patient to report any symptoms while the recording is occurring or soon thereafter. In another example, the WD, upon detection of an episode or an anomaly, may prompt the patient to record symptoms the patient may be experiencing. Alternatively, or in addition to the patient activating a button to request data recording, health data can be collected from other sensors or devices at the same time and can include vital signs information and/or symptom information, including at least one of the following—a heart rate, heart rate trend and/or histogram, spO2, temperature. Information about the wearer can also include wear compliance, steps taken, etc.

In some implementations, data blocks are stored for sub episodes for a period of time prior to a user triggered episode, such as 120 seconds prior to a detected health event, and/or post open of the user triggered episode. For example, the a user triggered episode may be uniformly 120 second long with a data block of 60 second prior to the user trigger and 60 seconds after the patient triggers the recording (opening). In other implementations, the user may also trigger the closing of the episode or the system may close the episode upon detection of particular health data meeting other end criteria. For example, if a duration threshold is not met for a certain data pattern or magnitude of the data, the episode may close. In some implementations, there may be a delay time, e.g., 2 seconds, between the user triggering of an episode the functional recording of the data block. Close of the episode may be triggered by the system detecting a stabilization of health data indicative of an event ending and end criteria being met.

FIG. 3B shows a scenario where the WD detects and initiates recording of an episode 310, for example a cardiac arrhythmia such as an SVT. The episode may be determined by the WD to be untreatable or treatable. A user independently activates a user triggered recording 312 of ECG after the WD detected episode recording is initiated.

The recordings of FIG. 3B may also include scenarios where the WD detects a treatable cardiac episode and delivers therapy, and a patient or a user also triggers a separate data episode after the WD episode detection. The patient triggered-record 312 is recorded in parallel with the WD Episode 310 and terminates before the WD episode terminates.

The display depicts the WD episode stitched together with the user triggered recording that are parallel and overlapping sub episodes, as a full episode 334. An overlapping portion 316 of the WD detected episode 310 and user triggered record 312 is stitched with a first portion 314 of WD detected episode 314 prior to the overlapping portion 316. A second portion 318 of WD detected episode 314 lasting after the close of the user triggered record 312 is stitched to the overlapping portion 316.

FIG. 3C illustrates a display of multiple stitched episodes, including WD detected episodes (Episode 1-5) and parallel overlapping user-triggered episodes (Triggered Record A, B, C). User triggered Episodes A 340 is spaced from a later user triggered Episode B 342 and an even later user triggered Episode 344. WD detected Episode 1 346 closes at the opening of WD detected Episode 2 348. WD detected Episode 3 350 closes at the opening of WD detected episode 4 352. WD detected Episode 5 354 occurs after Episode 4 352.

Stitched data blocks as shown on a display form a full episode 380 along a timeline 306. The full episode is made up of Episode 1 360 stitched with overlapping portion 362 to form user triggered record A, Episode 1 and Episode 2. A gap is provided between overlapping portion 362 and overlapping portion 366 formed by user triggered record B and Episode 3. Episode 4 368 is stitched in association with timeline 306 immediately after overlapping portion 366. Another gap 370 fills in the time between Episode 4 368 and overlapping portion 372. Overlapping portion 372 is formed by user triggered record C and a second portion of Episode 5 374. The remainder of Episode 5 374 is stitched to overlapping portion 372. The gaps 364 and 370 do not divide the full episode 380 but rather enables connection of episodes before and after the gap periods of time.

The medical monitoring device may detect an episode by monitoring and analyzing the captured health data stream. Various health events are presented by episodes that meet certain criteria that are specific to the health event. For example, known processes may be used by the monitoring device to correlate the health data to determine cardiac conditions may be employed.

In some implementations, the health data, such as an electrocardiogram, may include data obtained before an onset, throughout a duration, and/or post a conclusion of a clinically significant or otherwise predetermined as "of interest" cardiac episode or event, for example an abnormal arrhythmia, a brady or tachy event, an atrial fibrillation, a ventricular fibrillation, etc. A more complete representation and/or context of the episode can be assessed, given data just prior and post the episode can be captured, stored, and/or transmitted, or otherwise made available by the system to a reviewer.

In a specific example for illustration purposes, there may be five data blocks for significant health event(s). (1) onset of data, such as up to 120 seconds of data prior to an arrhythmia detection, (2) confirmation entry data, such as 60 seconds after the arrhythmia detection, (3) patent triggered recording, such as up to 120 seconds of data collected before and after the patient presses a button to start recording, (4) confirmation exit data such as final 60 seconds leading up to a detection of rate recovery or conversion, and (5) post closure data, such as up to 60 seconds of stored data after the detection of the rate recovery or conversion.

Figure 4A:
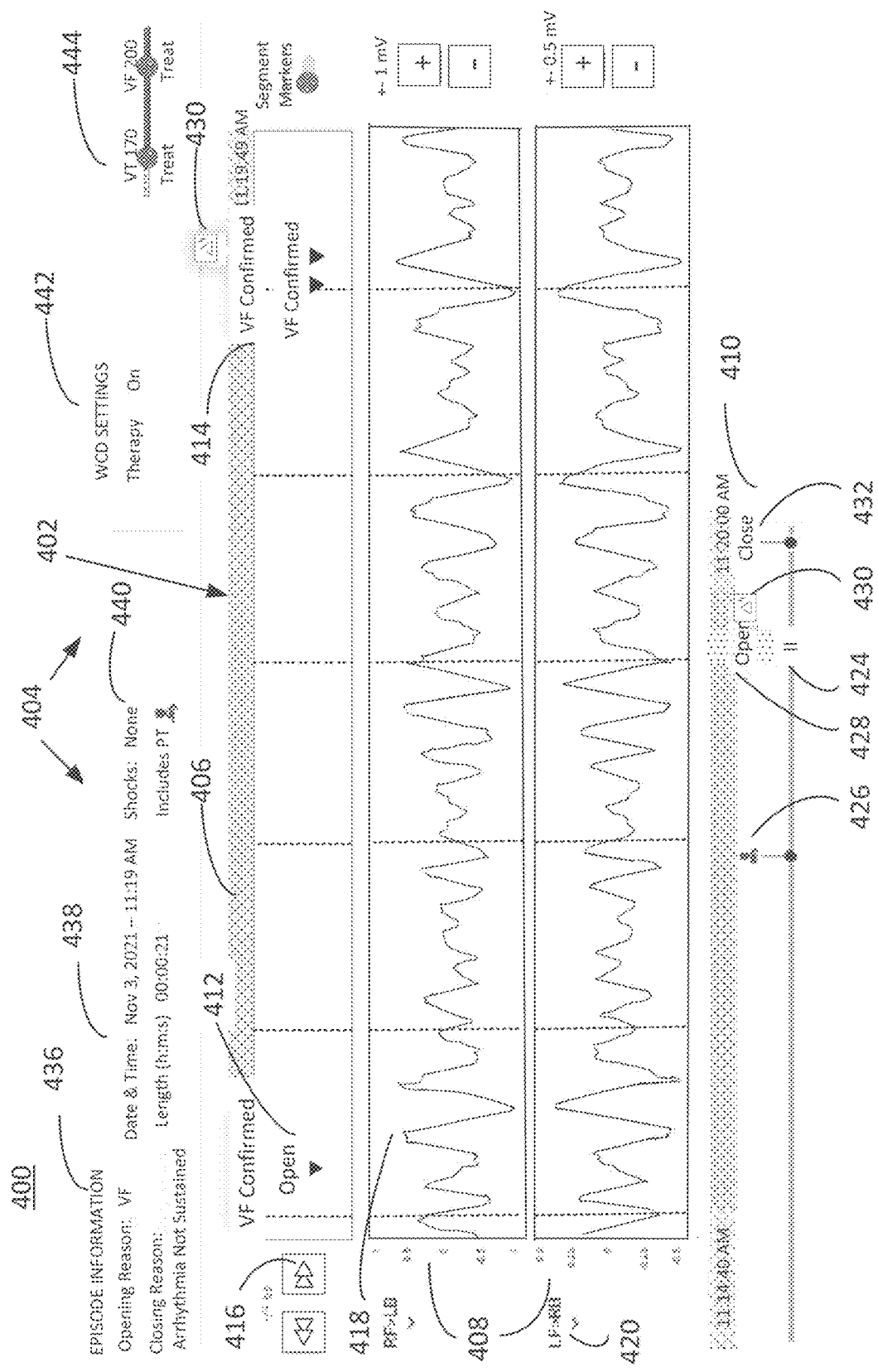
Figure 4B:
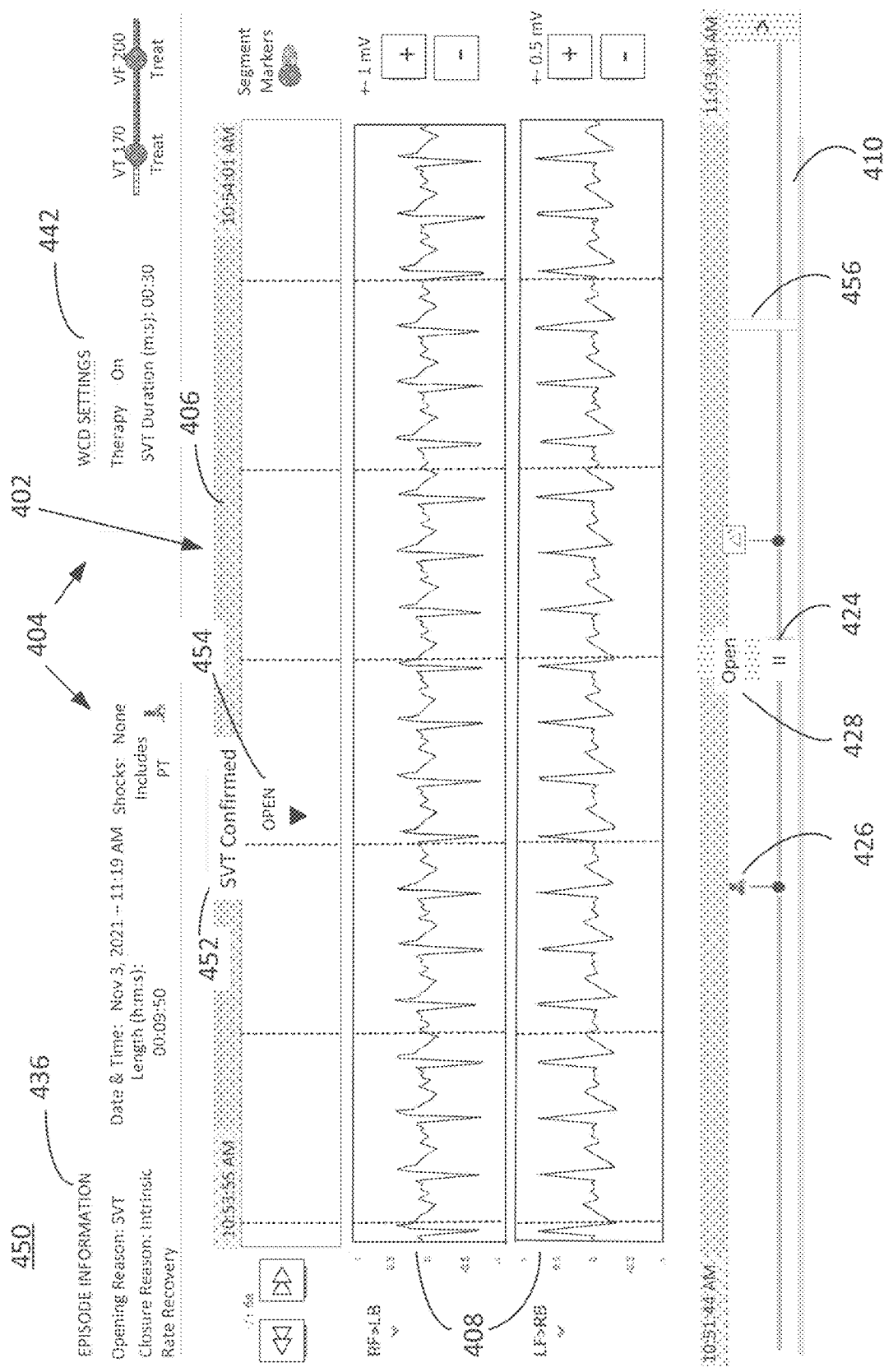
Figure 4C:
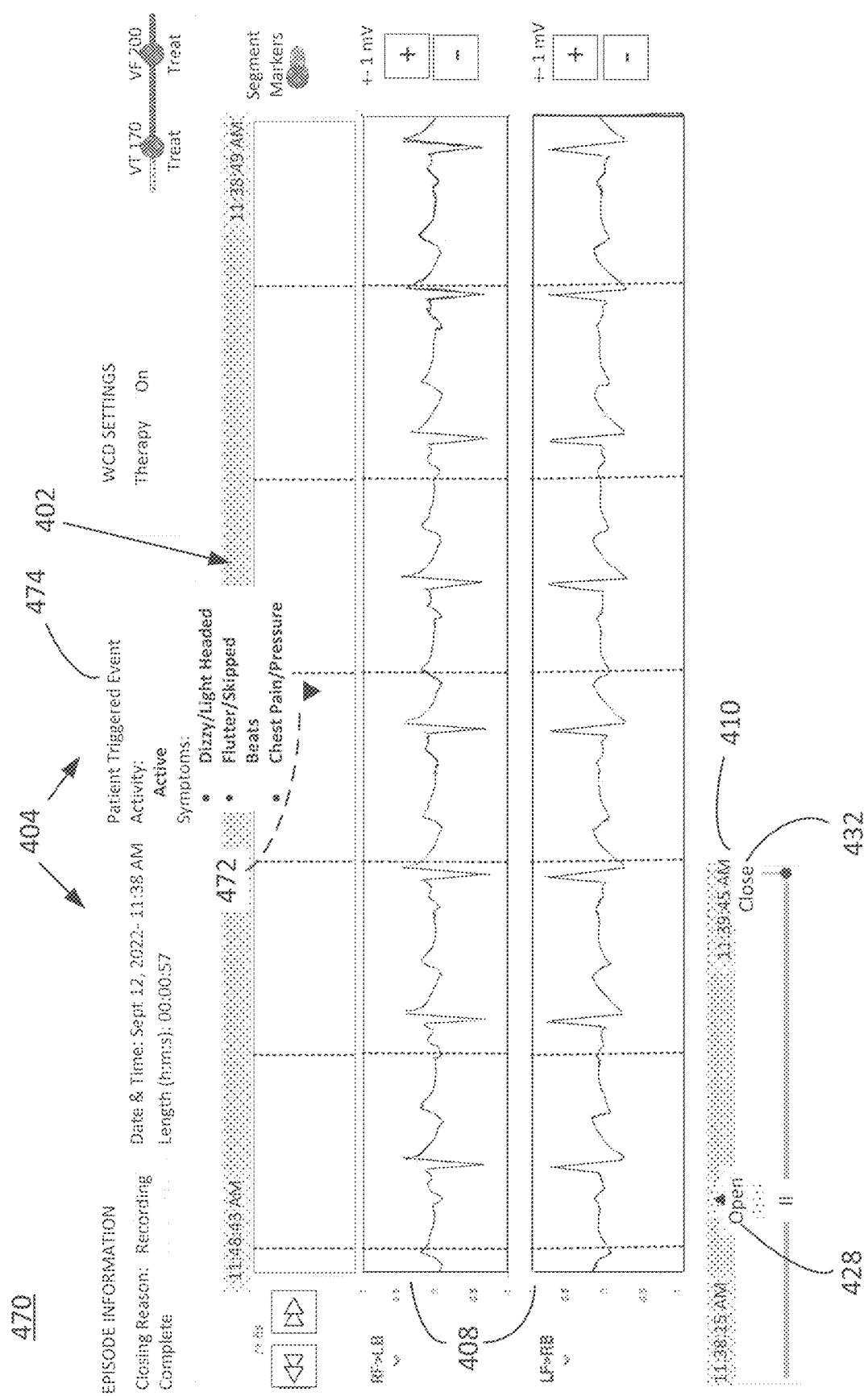

As shown variously in FIGS. 4A, 4B, and 4C, example data presentations are displayed on a user interface. FIG. 4A illustrates an example data presentation 400 that includes a data portion 402 and a background information portion 404.

In the example shown, the background information portion 404 is in a header location on top of the data presentation 400 and the data section is beneath. However, in various implementations, the background information section and data portion 402 may be in different positions on the data presentation.

The data portion 402 includes an episode view section 406, data graphs 408, and a health event section 410. The episode view section 406 includes a beginning time and an ending time that represent a concentrated focus period for data in data graphs 408. The episode view section 406 is aligned in time with the data graphs 408 in the focus period. The episode view section 406 includes graphical representations of episodes that are initiated at open points 412 which correspond with episode(s) in the data graphs 408. Graphical representations may indicate different data types depicted on respective timelines. Also shown are sources 414 of the episode opening, which in this case is "VF Confirmed", where the medical monitoring device confirmed that the data at the open point 412 meets criteria for VF. In some implementations, the display may show an "open" marking for the particular episode that embodies a confirmed event, rather than using an "open" marking for each episode.

Various control elements may be provided on the data presentation 400 to enable a reviewer to view select data and information and/or view the data and information in a particular way. For example, scroll element 416 is provided for a reviewer to shift the data forward or backward in time on the episode view section 406 and corresponding data graphs 408. The data presentation 400 may also include various control elements to jump to particular focus periods.

Data graphs 408 are ECG graphs 418 from two different channels, each channel data being depicted on separate graphs 408. For example, a data from a right front electrode/left back electrode channel are on a first graph and data from a left front electrode/right back electrode channel are shown on a second graph. A data source control element 420 enables a reviewer to select viewing of stored data from various sources. For example, a reviewer may select, e.g., from a drop down list, different electrode channels to view different data along the timeline of the data graphs section 408. In some implementations different numbers of data graphs may be provided, such as one or more than two.

In some implementations, the data presentation may display multiple data types or a same data type from various data sources (e.g., sensors) that generate signals representing various health parameters associated with the patient. Such different data may be display on the same timeline or separate timelines, but are related and stored in a single file as a full episode.

In some implementations, a same data source may be employed to acquire data representing different health parameters. For example, electrodes may obtain ECG data and also obtain respiratory data, such as impedance or DC signals. For example, data from a cardiac monitoring device and data from an spO2 device can be acquired substantially simultaneously as separate "sub episodes,", which when stitched together by the data management module are presented together on the display as one "full episode" that may be retrieved as a single record and each data type displayed on separate corresponding timelines of the data graphs section 418. Where various data types or data from different data sources are superimposed on a same timeline, the data individual graphs may have distinguishing features such as different colors and/or labels to identify the data type.

The health event section 410 of the data presentation 400 shows a zoom out summary of a complete timeline and episodes for the health event. The beginning time (e.g., 11:14:40 AM) and ending time (e.g., 11:20:00 AM) show that a longer period of time is depicted by the health event section 410 than the period of time of the episode view section 406 and data graphs 408. In some implementations, the health event section 410 may show a timeline and markings for episodes of multiple connected events. Thus, the health event section 410 may enable a convenient way of scrolling to view data from event to event or episode to episode along a timeline. The health event section 410 includes a focus period element 424 (e.g., "11") depicting the focus period shown by the episode view section 406 and data graphs 408.

The health event section 410 further includes graphical indications of episodes and the triggers for such episodes. An episode indicator 426 of a user triggered episode is shown along the timeline. In addition, episode indicator 428 represents an open point along the timeline, e.g., of a WD detected episode. Episode indicator 432 represents a close of the episode. The point in time of the open 428 corresponds in time with the open point 412 of the focus period in the episode view section 406. In this manner, episode opening and closure shown on the health event section 410 translate to the focus period of the episode view section 406.

In some implementations, episode indicators, such as user triggered opening 426 and WD detected opening 428 can include buttons that may be activated by the reviewer to control the view and shift the focus period of episode view section 406. Furthermore, sound icon 430 is shown on the timeline of the health event section 410 to show an audio message delivered by the medical monitoring system. For example, where a patient presses a button or holds the button, an audio message may be delivered to the patient.

The background information portion 404 provides for context information for the data. Episode information 436 may include a reason for opening the episode, e.g., VF detected or confirmed, and a reason for closing of the session, e.g., arrhythmia not sustained. In this example, a criterion for an episode requires that the data characteristic of the event, e.g., a pattern characterizing arrhythmia, be sustained for at least a threshold period of time, as a duration threshold. The criteria may also require a specified magnitude as a magnitude threshold for the data graphs to meet in addition to or instead of the time threshold, in order for a portion of data to qualify as a particular episode.

Time information 438 may provide a date and time of that the episode was initiated. The length of time from the open to the close of the episode may also be provided (e.g., 21 sec). In addition, episode feature information 440 may be provided, such as whether shock treatment was implemented, e.g., "none", and whether the data includes a patient triggered episode (e.g., "Includes PT").

General therapy setting information may be provided 442, such as "therapy on". A treatment key 444 for the patient may also be included on the data presentation 400. The treatment key 444 provides basic criteria in order for prescribed treatment to be activated, such as VT treatment takes place at 170 and VF treatment takes place at 200.

FIG. 4B is an example of a data presentation 450 that, like in FIG. 4A, includes a data portion 402 and a background information portion 404. Features labeled and described for the data presentation in FIG. 4A apply to same or similar features of FIG. 4B and labels may be incorporated by reference into FIG. 4B. Described are some of the aspects of FIG. 4B that may be different than FIG. 4A.

The episode view section 406 of FIG. 4B includes an open point 454 of an episode that indicates the point along the data graphs 408 in which an episode is opened. The episode view section 406 also shows the source 452 of the episode opening, which in this case is "SVT Confirmed" where the medical monitoring device, e.g., WD, confirmed that the data at the open point 452 meets criteria for SVT.

The health event section 410 of FIG. 4B shows an episode indicator 426 of a user triggered episode along the timeline and an open episode indicator 428. The focus period element 424 depicts the section of the longer timeline of the health event section 410 that corresponds with the shorter focus period of the episode view section 406 and data graphs 408, e.g., time period between 10:53:55 AM to 10:54:01 AM.

The background information portion 404 of FIG. includes episode information 436 with a reason for opening the episode as SVT and reason for closing as intrinsic rate recovery, as detected by the medical monitoring device by assessing the incoming health data.

Therapy setting information 442 shows that "therapy setting is on. Episode duration time is also provided, e.g., SVT Duration time of 30 seconds. In some health events, an episode must be maintained for a specific duration to trigger treatment. For example, data indicating an SVT may need to be sustained continuously for a specific length of time to be considered a VT as a treatable episode, which then activates treatment protocols.

The description of components and features described above with regard to FIG. 4A apply to similar components and features shown and not described specifically for FIG. 4B.

FIG. 4C is an example of a data presentation 470 with only an episode that is manually triggered and closed by a user, such as the patient, along with supplemental information entered by the user. The data presentation of FIG. 4C includes a data portion 402 and a background information portion 404. Features labeled and described for the data presentation in FIG. 4A apply to same or similar features of FIG. 4C and labels may be incorporated by reference into FIG. 4C. Described are some of the aspects of FIG. 4C that may be different than FIG. 4A.

The episode view section 406 of FIG. 4C includes an episode indicator of a user triggered opening 472 (dashed lead line), which is covered in the current view of the data presentation by a symptoms pop-up window 474. The episode indicator 472 may include a button, which when activated by the user, such as by clicking on the episode indicator 472, causes the symptoms window 474 to appear.

Symptoms window 474 includes a status of the patient triggered event, e.g., "active." A list of user entered symptoms are also provided in symptoms window 474, such as "Dizzy/Light Headed", "Flutter/Skipped Beats" and "Chest Pain/Pressure." The symptoms are experience and recognized by the patient as potentially indicative of an episode of a health event. In some implementations, a user may trigger opening and closing of an episode without experiencing symptoms but for other reasons. The symptom window along the timeline corresponds with a time that the symptoms are entered into the system.

As shown in health event section 410 of FIG. 4C, the episode was opened 428 and then closed 432 shortly after being opened and the event ended upon close. The description of components and features described above with regard to FIGS. 4A and 4B apply to components and features labeled and not specifically described for FIG. 4C.

While the above-described implementations are directed to monitoring systems for cardiac monitoring and capturing ECG data, other implementations include medical systems having one or more implanted sensors for which ECG and/or other physiological waveform data is collected and can be displayed. In view of the present disclosure, the above-described implementations of a user interface for capture and display of data can be adapted for waveforms other than ECG. For example, such data can include but are not limited to: electroencephalogram (EEG), capnography, electrodermal activity (EDA), transthoracic impedance (TTI), photoplethysmography, SpO2, heart-sound/phonocardiogram, electromyography (EMG), etc. Implementations enable a user to control a user interface to capture and/or select a portion of data. The user can then, for example, use the user interface to concurrently display the baseline/comparator with other waveforms or other portions of the same waveform for comparison.

Figure 5A:
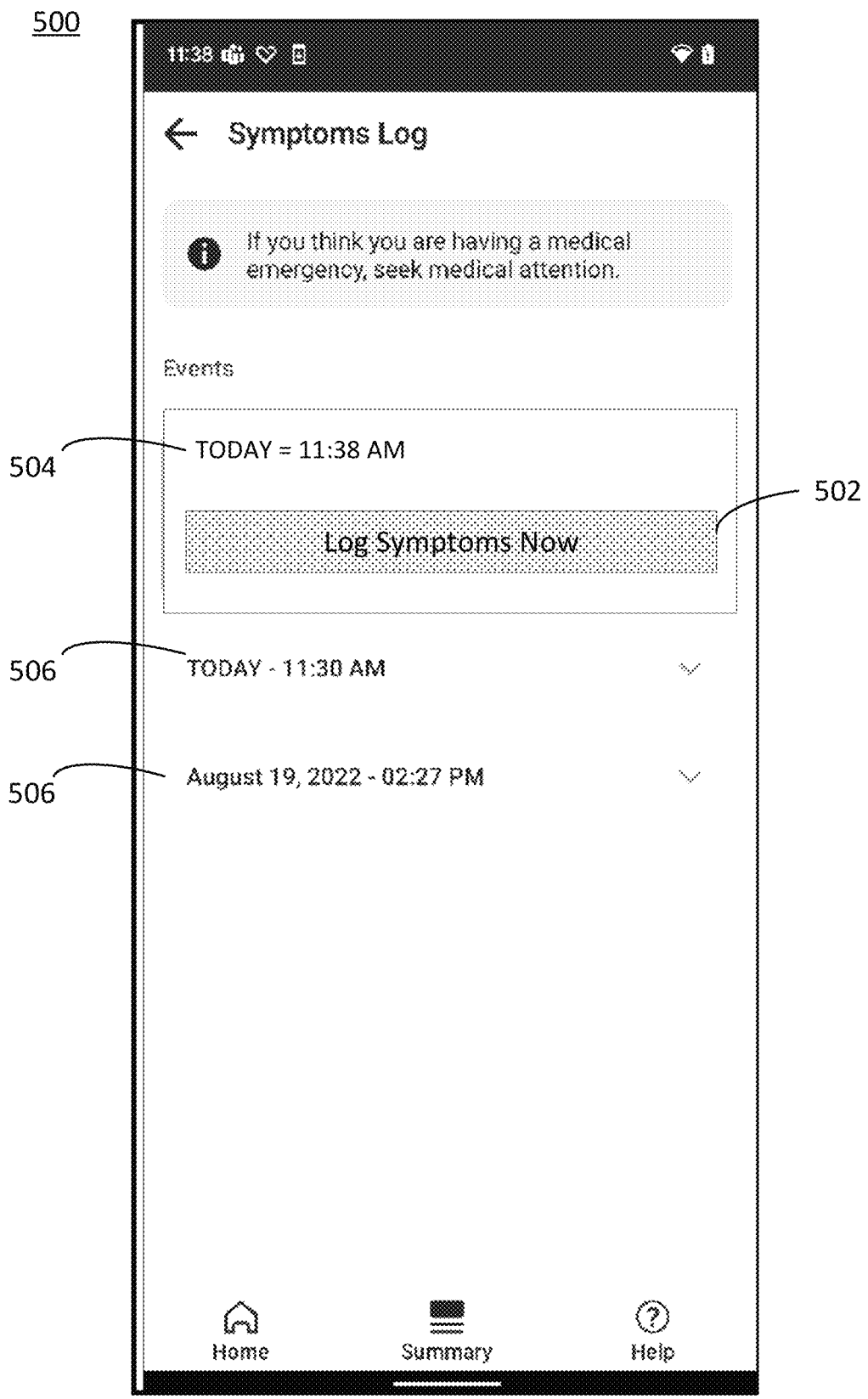
Figure 5B:
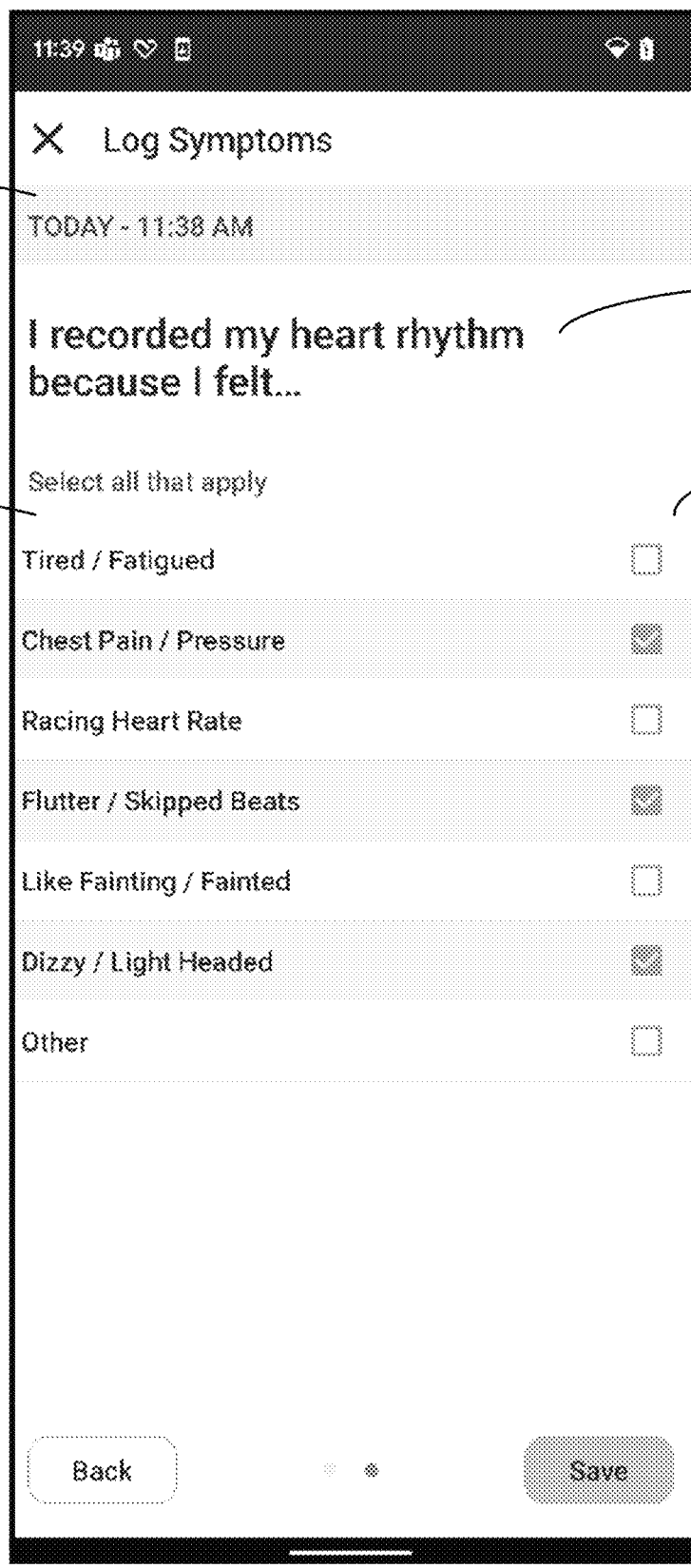

FIGS. 5A and 5B show example user interfaces for a user to enter supplemental information to the medical data management system, for example, accessed on an assistant device. The user interfaces 5A and 5B may be accessed through a health monitoring application for example downloaded onto the assistant device, via a website as a Tillable form, by the user logging into a dedicated health portal, etc.

At times, the patient or other user may be prompted to access the user interfaces 5A and/or 5B. For example, the assistant device and/or medical monitoring device may signal via a unique sound, light, vibration, etc. to indicate to the patient that it is time to enter symptoms. In some implementations, the prompt may occur in response to the user or the WD triggering the opening of an episode. For example, the assistant device and/or medical monitoring device may output a voice that verbally requests entry of the information.

Entry of the supplemental information may be through various input mechanisms, which may include, without limitation, touchscreen, switch input with an on-screen or external keyboard, head mouse, voice recognition, gesture recognition, facial recognition, movement tracker, eye movement tracker, smart buttons, trackball, track pen, pen tablet, pen, stylus, and hand mouse. The input may rely upon a user applying touch, voice, click, tap, type, gestures, movement (e.g. moving an eye, arm, body), and other actions. In some implementations, a user contacts the display screen showing the user interface using a finger or stylus in order to select items displayed by the display screen. The user may enter text, such as in an "other" field, or activate control functions of the display screen.

FIG. 5A is an example of a symptoms start screen 500. A link box 502 is provided to navigate to an entry screen 520. An entry time 504 is the current time, which is recorded as an entry time for input of the symptoms. The entry time 504 may be associated with a corresponding episode to be stored with the full episode or otherwise identified as part of the full episode for display with the full episode on the data presentation.

A log 506 of previous symptom log entries is provided identified by the entry date. The log 506 includes a drop down element that the user may click on to view the symptoms previously entered for each log entry.

FIG. 5B is an example of a symptoms entry screen 520. The symptoms entry screen 520 includes instructions 522 to the user on entering symptoms. A list of symptoms 524 are displayed from which the user may select the symptoms that pertain to the patient by selecting the corresponding check box elements 526. The entry time 504 is provided.

FIG. 6 shows a flowchart of an example data management process 600 to stitch and data blocks for a data presentation. The data management process is performed by components of the medical data management system, for example as described with reference to FIG. 1.

In block 602, health data is acquired from a patient by a medical monitoring device, such as a wearable device (WD). The health data is monitored as patient parameters that potentially relate to a health even of the patient. For example, the health data may include ECG data, respiratory data, sleep period data, oxygenation level data, etc. The health data may be acquired as a continual stream of data during the monitoring time.

In block 604, the health data is monitored to determine initiation of a health episode associated with the health event. In decision block 606, it is determined whether the health data meet initiation criteria indicative of the health event or significant episode. The health data is assessed against criteria that specifies a particular health event, such as by analyzing data for heart rhythms, which can include use of techniques known in the field. In some implementations, a particular waveform may need to be sustained for a designated period of time and/or be of a specific magnitude and/or shape. The overall rhythm as represented by the health data may be classified, e.g., VF, VT, Slow VF, SVT, Asystole, Bradycardia, or Noise. Such analysis may be performed by one or more algorithms employed by the medical data management system.

Decisions may also be made as to whether an episode is treatable. For example, a decision to inject a shock to a patient may be based on a heart rate above the programmed rate threshold and the R-wave duration. A shock may be only provided in the case of a VT, slow VF or VF but not in the case of an SVT, as distinguished by the width of the R-wave. After a shock treatment, a reviewer may continue to monitor the health data for example to determine if another shock treatment is required. Thus, data blocks from post treatment may be stored for analysis.

If the episode criteria are not met by the currently incoming health data, the process returns to block 604 to continue to monitor and evaluate the incoming health data. Should the episode criteria be met, an episode is opened and recording of the episode commences in block 606. This step 606 begins the specifying of a data block for the episode.

In some implementations, the medical data management system may employ a neural network to determine whether a health episode is implicated by the health data. For example, the neural network may receive as input various health data of patients. The neural network processes the data to output a prediction that incoming health data indicate an episode has begun for the patient. The neural network may be trained with health data of various combinations of episodes for different health events that together indicate a high probability of a particular episode. Feedback data may be attained by confirmation of a health event episode, for example by a clinician confirming the presence of an episode in reviewing the input health data. Such feedback data may be used as training input data to re-train the neural network.

The medical system continues to monitor the incoming health data. In decision block 610, it is determined whether the health data still meets the episode criteria. If the criteria is still met, the process repeats to determine whether the health data meets the criteria in block 610. If end criteria is met (e.g., initiation criteria is no longer being met by the data), at that point in block 612, the episode is closed and specifying of the data block is complete. The data block is recorded as an independent clip of data, stored in individual files prior to stitching of the data blocks into a single file for a full episode.

In some implementations, the data block is transferred from one device, such as the medical monitoring device, to one or more data management devices to conduct one or more of subsequent steps described below. However, in some implementations, a single device may perform all of the steps of the data management process 600.

In some implementations, data blocks are assessed to determine a relationship between one or more data blocks. The relationship may be based on portions of a single episode, multiple episodes related in time, related to a health event, or other predefined relate criteria. For example, multiple episodes, which may be recorded in parallel and/or overlapping, may be opened and closed by different trigger mechanisms, such as WD episode detection and user triggered. In further examples, multiple data sources may be acquiring data indicative of an episode, where the data may be of the same, e.g., ECG from multiple electrode channels, or different data type, e.g., ECG from an electrode channel and spO2 from an spO2 device. The related data blocks may be clustered into a data group and individual data block files may be collectively transferred, or otherwise marked as belonging to a same group, to be provided to another device for continued processing.

In some implementations, different types of health data from different sources may be related to each other via a common health event. The different types of data may be aligned in time, for example, by a time stamp for the time of acquisition of the data. In some implementations, the system may use a delta change in time, such as 5 seconds difference, between data from distinctive sources to compensate for different times that the data is acquired, transferred, and/or processed due to, for example, the nature of different devices, modes of transfer, and/or types of data (e.g. multimedia files may be slower to transfer than numerical or text files).

In some implementations, supplemental information is acquired from secondary sources not retrieved by sensors of the medical monitoring device. For example, a user may input symptoms or other observations or comments regarding a recorded episode. Such supplemental information may also be grouped with related data blocks or provided as separate information related to the data blocks by time or an identifier.

In block 612, the related data blocks for sub episodes are stitched according to a timeline to form a full episode that is stored as a single episode file. For example, the data blocks are stitched in order and according to time of the respective opening and closing of sub episodes with possibly some overlapping portions, along a timeline. In some implementations, a stored full episode may be "de-stitched" to retrieve, upon request, the original sub episodes into separate files to review separate sub episodes.

In block 614, the stitched data blocks are provided to a rendering module associated with a display to be rendered in a data presentation. The data presentation has one or more timelines and graphic representations of the stitched data blocks. In some implementations, any related supplemental information is also provided for rendering on the data presentation with indication of the relationship of the supplemental information to the corresponding time of the full episode.

Some or all of the process 600, or any other processes described herein, or variations and/or combinations of those processes, may be performed under the control of one or more computer systems configured with executable instructions and/or other data, and may be implemented as executable instructions executing collectively on one or more processors. For example, the process 600 may be adapted to include steps for treating a patient, such as a defibrillator shock based on the determined episodes. The process 600 may be also adapted to include steps to include indications of treatment in the data presentation according to the time of the treatment.

As shown in FIG. 7 shows an example of the medical monitoring device 700 (referred to as the wearable device) configured for patient wear that may be implemented in the medical data management system. The wearable device 700 has a vest type garment support structure 702 that houses various components, one or more external signal source components 742 that are not housed by the support structure, and a main unit 720 in communication with the support structure 702.

Components held by the support structure 702 may include one or multiple electrodes 704. The support structure 702 may also contain a hub 708 to communicate with the various signal source components of the support structure 702, as well as communicate with one or more external signal source components 742, such as an oximeter, not housed by the support structure 702. The hub 308 may further communicate with the main unit 720.

Additional signal source sensors 750 that may be housed by the support structure 702 may include an audio detector such as heart-sound/phonocardiogram, patient temperature thermometer, GPS, pressure sensors, optical sensors such as photoplethysmography, etc. to produce signals used in generating health data about the patient. A microphone may be positioned to detect frequency, volume, intensity, regularity, etc. of heart beat. The microphone may also detect frequency, volume, regularity, etc. of breaths. Such additional signal source sensors 750 may be wired or wirelessly coupled to hub 708 to provide signals produced by the additional signal source sensors 750 according to the sensors sensing of parameters of the patient.

External signal source component 742 may be attached to other parts of the patient, for example, which may be more conducive to sensing a physiological parameter rather than at the torso. An example external signal source component 742 may include an oximeter (also referred to as an "SpO2 sensor") engaged with a body part, such as a finger, of the patient in which blood flow is easily detected. The oximeter may detect a reduction in blood oxygen level and signals or health data from the oximeter can be time-synchronized with other health data, such as the ECG and respiration data. Reduced blood oxygen saturation level may indicate a respiratory disturbance of the patient.

The hub 708 can receive data from the external signal source component 742 and transfers instructions or activation signals to the external signal source component 742 via wired cable connection and/or a wireless communication mechanism. In some implementations, an external signal source component 742 may transfer signals directly to main unit 720 rather than to hub 708.

Electrodes 704 are removably fixed to an inside of the support structure 302 to make contact with the skin of the patient directly or through a conductive medium, such as an electrolyte. The electrodes 304 may be electrically coupled to main unit 320 or to the hub 308 via electrode cable 722. The electrodes 704 may be functional as both therapy and monitoring electrodes, or just monitoring electrodes without therapy functionality. Electrodes 704 may be configured to produce electrical signals for ECG data and/or respiration data, e.g., AC signals for respiratory impedance determination, or DC signals.

In some implementations, the main unit 720 may receive signals or data from the hub 708 and perform computations to determine whether the patient experiences a health event, such as a cardiac anomaly, assess incoming health data, specify data blocks to open and close an episode, determine related data blocks to form data groups, transmit the processed data to the assistant device and/or remote computing device to further process, store and display data blocks.

The support structure shown in FIG. 7 illustrate a vest type garment wearable medical monitoring device. In some implementations, the medical monitoring device may take various forms or combination of forms. For example, the wearable structure may include one or more patches, one or more bands, and/or a torso fitted garment to house various components of the medical monitoring device.

Figure 8:
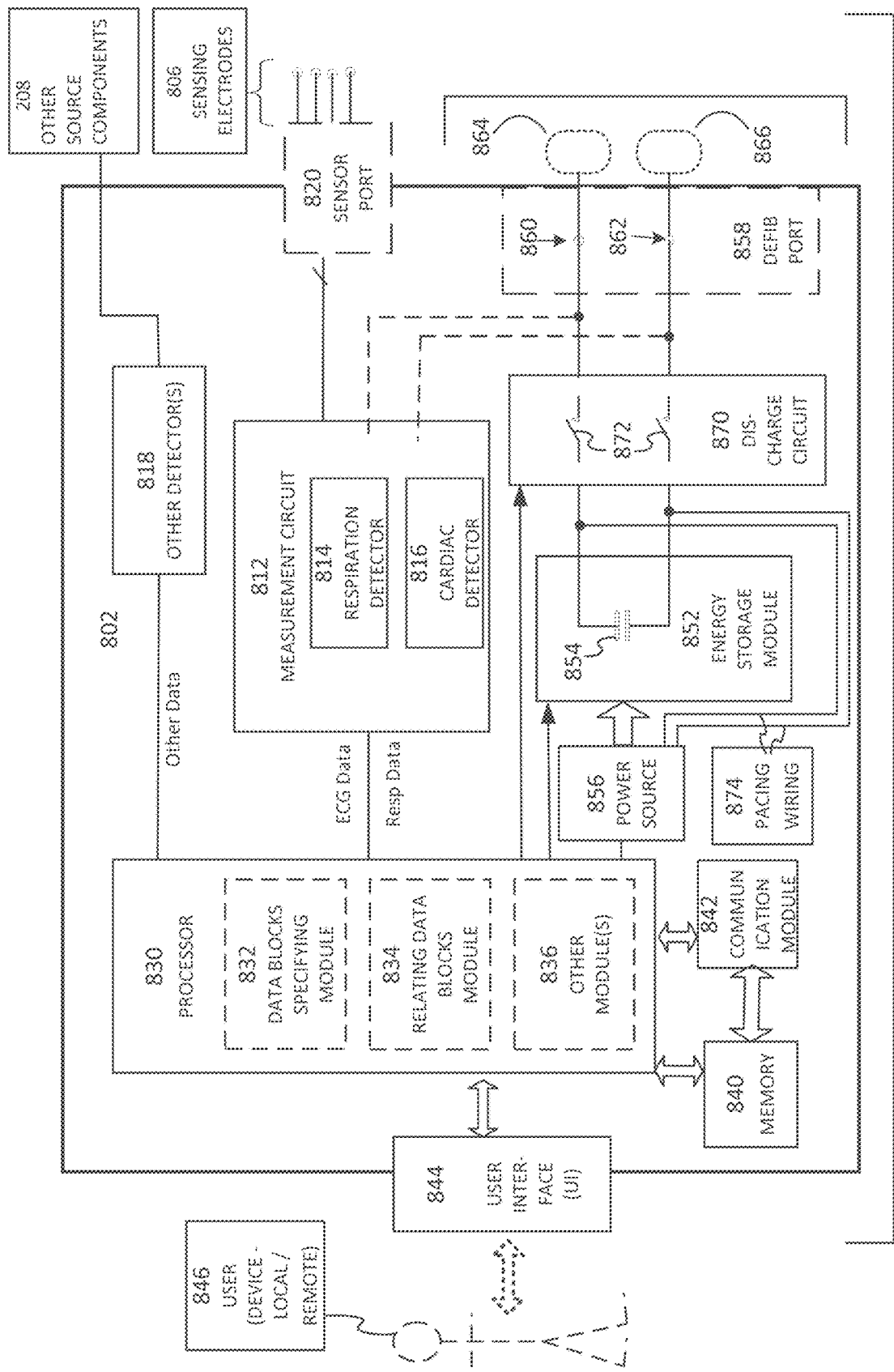
FIG. 8 is a block diagram illustrating an example of components of a medical monitoring device upon which data acquisition and assessment to specify data blocks may be implemented, in accordance with some implementations.

FIG. 8 shows an example medical monitoring device 800 employs a variety of sensors, transducers, and/other source components to generate and/or transfer health signals associated with the patient to unit 802 of the monitoring system 800. The unit 802 is intended to represent one or more units that perform functions on health signals or health data. Functions of the unit(s) can include one or more of collect signals representing various health parameters relevant to the health of a patient from signal source components generate health data associated with the signals, determine potential or actual health events, assess health data to specify data blocks, store data blocks, determine relationships between data blocks, and output data blocks. The unit 802 may also perform additional functions and combinations of these functions.

In some implementations, the functions of unit 802 may be entirely performed by a single unit, such as a main unit 720 in FIG. 7. In other implementations, particular functions represented by unit 802 may be shared between two or more units, such as a hub 708 in FIG. 7 and the main unit 702.

Signal source components include sensors and/or transducers, to collect health signals associated with health parameters relevant assessing the patient for health events. Health parameters may include any combination of patient physiological parameters, patient state parameters, system parameters, and environmental parameters. Other types of signal source components are possible, including clocks to track time and date. Signals from the various source components feed into detectors for processing and generating of associated health data.

Sensing electrodes 806 may produce signals for ECG interpretations and for respiration assessments. Sensing electrodes 806 may be one or more transducers configured to acquire electrical signals indicative of heart activity, such as ECG signals and respiratory signals, e.g., impedance signals from variating AC current and DC current signals. Unit 802 may optionally have at least one sensor port 820. The ECG of the patient can be sensed as a voltage difference between sensing electrodes 806.

In some implementations, unit 802 also includes a measurement circuit 812 to receive one or more electrical physiological signals of the patient from sensor port 820. Sensing electrodes 806 produce heart activity related signals, such as ECG signals and respiratory signals, which are fed into a corresponding cardiac detector 816 and/or respiratory detector 814 of a measuring circuit 812 to generate ECG and/or respiration data.

Electrical signals in the form of impedance signals may be fed as input to the respiratory detector 814 of the measurement circuit 812 to determine impedance respiratory data. Impedance can be sensed between electrodes 806 and/or the connections of sensor port 820. In implementations, respiratory detector 814 may be configured to render impedance respiratory data of the patient based on received impedance AC signals that can be rendered as a modulation to a carrier signal, as a stream of values, and so on. The measurement circuit 812 can render or generate health data about the received signals.

Examples of other signal source components 808 may include sensors or transducers such as a perfusion sensor, a pulse oximeter, a device for detecting blood flow (e.g. a Doppler device), a sensor for detecting blood pressure (e.g. a cuff), an optical sensor, illumination detectors and sensors working together with light sources for detecting color change in tissue, a device that can detect heart wall movement, a sound sensor, a device with a microphone, a Saturation of Peripheral Oxygen ($SpO_2$) sensor, a GPS for example used to determine a sudden cardiac arrest or other cardiac conditions, and so on. Signals from the other signal source components 808 may be inputted into the cardiac detector 816, respiratory detector 814, and/or other detector(s) 818.

The health data is processed by the processor 830 of the medical monitoring device 800. In some implementations, processor 830 may include intelligent hardware, e.g., a central processing unit (CPU), a microcontroller, an application specific integrated circuit (ASIC), etc. The processor 830 may be implemented in a number of ways. Such ways include, by way of example and not limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 830 may include, or have access to, a non-transitory storage medium, such as a memory 840. The memory 840, which can work together with processor 830. Memory 840 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 840 is thus a non-transitory storage medium. Memory 840 can include programs for processor 830, which processor 830 may be able to read and execute. More particularly, the programs can include sets of instructions in the form of code, which processor 830 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made.

Memory 240 may be employed to store data, such as health data. This data can include patient data, system data and environmental data, for example as learned by the various source components. The data can be stored in memory 840 before it is transmitted out of unit 802, or stored there after it is received by unit 802.

Processor 830 can be considered to have a number of modules. In some implementations, and as a matter of convention used herein, instances of the software may be referred to as a "module" and by other similar terms. Generally, a module includes a set of the instructions so as to offer or fulfill a particular functionality. Implementations of modules and the functionality delivered are not limited by the implementations described in this document.

One such module can be a health determination module 832 to determine a variety of actual or potential health disorders including those health disorders discussed above such as cardiac conditions and sleep disorders. For example, data block specifying module 832 may implement logic to determine data blocks indicative of an episode of a health event based, at least in part, on the acquired health data.

Relating data blocks module 834 of processor 830 may assess data blocks to determine a relationship to group the data blocks, such as relating to a particular health event. Data blocks that form a data group may be maintained in individual files and may be marked as relating to each other.

The processor 830 can also include additional modules, such as other module 836, to perform other functions for multiple purposes. For example, the other module 836 may operate particular source components or other devices. Other modules 836 may organize the health data in particular ways, such as trend data that may be transferred to the data management device(s).

Unit 802 includes a communication component for establishing one or more wired or wireless communication links with other devices of the medical data management system. The communication component may include various hardware and/or software elements, such as a communication module 842 and/or user interface 844.

The communication module 842 may also include software that enables communications of the user interface 844 over a network such as the HTTP, TCP/IP, RTP/RTSP, protocols, wireless application protocol (WAP), IEEE 902.11 protocols, and the like. In addition to and/or alternatively, other communications software and transfer protocols may also be used, for example IPX, UDP or the like. The communication network may include a local area network, a wide area network, a wireless network, an Intranet, the Internet, a private network, a public network, a switched network, or any other suitable communication network, such as for example cloud networks. The network may include many interconnected computer systems and any suitable communication links such as hardwire links, optical links, satellite or other wireless communications links such as Bluetooth, Wi-Fi, wave propagation links, or any other suitable mechanisms for communication of information. For example, the network may communicate to one or more mobile wireless devices, such as mobile phones, tablets, and the like, via a base station such as a wireless transceiver.

User 846 may include a person and/or computing system, such as the assistant device 110 of FIG. 1 and/or the data management device 120 of FIG. 1. For local interaction with the medical monitoring system 800, the user 846 may include the patient or a local bystander, such as the. In some implementations, the user 846 may be a remote entity, such as the assistant device of a remote person or a medical server device. For example, the user 846 may be a health support entity such as a doctor, caregiver, other health care provider, health care service, dispatch, technical service, an authorized person, and so on, including combinations thereof. The user may also include a medical server device or devices such as a cloud service, serving as a repository for health data of the patient.

A user interface 844 may transmit information to the user 846 and in some implementations may receive information from the user 846. The user interface 844 may be configured to send and receive data and information, for example, according to transfer link 106 in FIG. 1.

In some implementations, health data, e.g., in the form of data blocks and/or data groups, may be pushed to the user 846 at predesignated times or intervals. The information may also be pulled to user 846 by requests for information sent to the unit 802 by user 846 or other authorized parties, for example according to the Health Insurance Portability and Accountability Act of 1996 ("HIPAA") or other privacy regulations, to access the information.

In some implementations, the medical monitoring device 800 can be configured to provide cardiac treatments directly to the patient, such as defibrillating the patient, in addition to monitoring health parameters. Defibrillation can be performed by defibrillate components of the monitoring system delivering an electrical charge to the body of the patient in the form of an electric shock. The electric shock can be delivered in one or more pulses.

An energy storage module 852 temporarily stores electrical energy in the form of an electrical charge, when preparing for discharge of a pulse to administer a shock. In implementations, energy storage module 852 can be charged from a power source 856 to a designated amount of energy, as controlled by processor 830. In typical implementations, energy storage module 852 includes a capacitor 854, which can be a single capacitor or a system of capacitors, and so on. In some implementations, energy storage module 852 may include a device that exhibits high power density, such as an ultracapacitor. Capacitor 854 can store the energy in the form of an electrical charge, for delivering to the patient.

Based on the findings of a cardiac event by the processor 830, the processor 830 may further determine that treatment is warranted. In some implementations, the processor 830 may determine treatment based on additional information as well, such as patient medical history data, event history data, etc. The processor 830 may activate discharge circuit 870 to deliver an appropriate shock treatment to the patient. In some implementations, when the determination is to shock, an electrical charge pulse is delivered to the patient. Delivering the electrical charge is also known as discharging. Shocking can be for defibrillation, pacing, and so on.

Defibrillation port 858 includes electrical nodes 860, 862. Leads of defibrillation electrodes 864, 266 can be plugged into defibrillation port 858, so as to make electrical contact with nodes 860, 862, respectively. It is also possible that defibrillation electrodes 864, 866 are connected continuously to defibrillation port 858, instead. Either way, defibrillation port 258 can be used for guiding, via electrodes, the electrical charge that has been stored in an energy storage module 852, to the patient.

Discharge circuit 870 can include one or more switches 872, which may also include one or more bridges. Switches 872 can be made in a number of ways, such as by an H-bridge, cross-bar switch, or other switching mechanisms to control current flow. Discharge circuit 272 can also be controlled by a user or external computing device via user interface 844. Measuring circuit 812 can further monitor the amount of electrical current provided from the discharge circuit 872 prior to release to the patient.

When the defibrillation electrodes 864, 866 make sufficient electrical contact with the body of the patient, the unit 802 can administer, via the defibrillation electrodes 864, 866, a brief, strong electric pulse through the body. The pulse is also known as defibrillation pulse, shock, defibrillation shock, therapy, electrotherapy, therapy shock, etc. The pulse is intended to go through and restart the heart, in an effort to save the life of the patient. The defibrillation pulse can have an energy suitable for its purpose, such as at least 100 Joule ("J"), 200 J, 300 J, and so on.

In some implementations, defibrillation electrodes 864, 866 may be multi-functional to also provide electrical signals to measurement circuit 812 to generate ECG data and/or respiratory data. In such implementations, the medical monitoring device system 800 may include both defibrillation electrodes 2864, 866 and sensing electrodes 806, or may include the multi-functional defibrillation electrodes 864, 2866 without also dedicated sensing electrodes 806.

In some implementations, cardiac treatment may include providing a pacing pulses with energies similar to pacers rather than defibrillators, if processor 830 determines that pacing is appropriate according to the health data. For pacer implementations, at least some of the stored electrical charge can be caused to be discharged via at least two of the defibrillation electrodes 864, 866 through the patient, so as to deliver to the patient a pacing sequence of pacing pulses. The pacing pulses may be periodic, and thus define a pacing period and the pacing rate. There is no requirement, however, that the pacing pulses be exactly periodic. A pacing pulse can have an energy suitable for its purpose, such as at most 100 J, 25 J, usually about 10 J, and so on. In either case, the pulse has a waveform suitable for this purpose.

When the decision of the determination module 832 is to provide electrical discharge in the form of a pace, i.e., to deliver pacing pulses, the processor 830 can be configured to cause control the discharge circuit 870 to discharge through the patient at least some of the electrical charge provided by the power source 856. Since pacing requires lesser charge and/or energy than a defibrillation shock, in some implementations, pacing wiring 874 is provided from the power source 856 to the discharge circuit 870.

Figure 9:
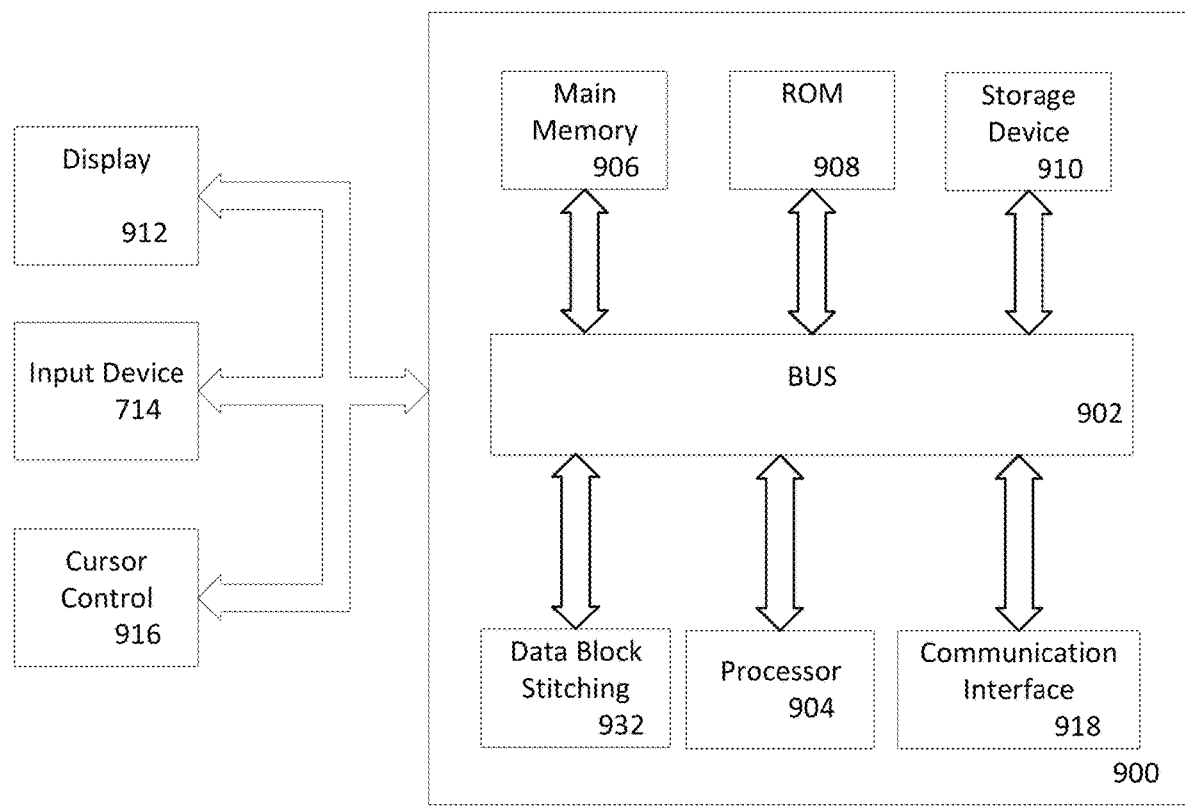
FIG. 9 is a block diagram illustrating an example computer system upon which stitching and display of data may be implemented, in accordance with some implementations.

FIG. 9 shows an example computing device, such as remove data management device 120 in FIG. 1, which may implement data management processes described herein. The computer system 900 includes a bus 902 or other communication mechanism for communicating information, and a processor 904 coupled with the bus 902 for processing information. The processor 904 may be, for example, a general purpose microprocessor.

In some implementations, the computer system 900 may include data block stitching module 932 to stitch related data blocks for combined storage and ready access to provide to a display 912.

The computer system 900 also includes a main memory 906, such as a random access memory (RAM) or other dynamic storage device, coupled to the bus 902 for storing information and instructions to be executed by the processor 904. The main memory 906 may also be used for storing temporary variables or other intermediate information during execution of instructions to be executed by the processor 904. Such instructions, when stored in non-transitory storage media accessible to the processor 904, render the computer system 900 into a special-purpose machine that is customized to perform the operations specified in the instructions.

The computer system 900 further includes a read only memory (ROM) 908 or other static storage device coupled to the bus 902 for storing static information and instructions for the processor 904. A storage device 910, such as a magnetic disk or optical disk, is provided and coupled to the bus 702 for storing information and instructions.

The computer system 900 may be coupled via the bus 902 to the display 912, such as a computer monitor, for displaying the data presentation. An input device 914, including alphanumeric and other keys, is coupled to the bus 902 for communicating information and command selections to the processor 904. Another type of user input device is a cursor control 916, such as a mouse, a trackball, or cursor direction keys for communicating direction information and command selections to the processor 904 and for controlling cursor movement on the display 912.

The computer system 900 may implement the techniques described herein using customized hard-wired logic, one or more ASICs or FPGAs, firmware and/or program logic which in combination with the computer system causes or programs the computer system 900 to be a special-purpose machine. According to one implementation, the techniques herein are performed by the computer system 900 in response to the processor 904 executing one or more sequences of one or more instructions contained in the main memory 906. Such instructions may be read into the main memory 906 from another storage medium, such as the storage device 910. Execution of the sequences of instructions contained in the main memory 906 causes the processor 904 to perform the process steps described herein. In alternative implementations, hard-wired circuitry may be used in place of or in combination with software instructions.

The term "storage media" as used herein refers to any non-transitory media that store data and/or instructions that cause a machine to operate in a specific fashion. Such storage media may include non-volatile media and/or volatile media. Non-volatile media includes, for example, optical or magnetic disks, such as the storage device 910. Volatile media includes dynamic memory, such as the main memory 906. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, an EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire, and fiber optics, including the wires that include the bus 902. Transmission media can also take the form of acoustic or light waves, such as those generated during radio-wave and infra-red data communications.

Various forms of media may be involved in carrying one or more sequences of one or more instructions to the processor 904 for execution. For example, the instructions may initially be carried on a magnetic disk or solid state drive of a remote computer. The remote computer can load the instructions into its dynamic memory and send the instructions over a network connection. A modem or network interface local to the computer system 900 can receive the data. The bus 902 carries the data to the main memory 906, from which the processor 904 retrieves and executes the instructions. The instructions received by the main memory 906 may optionally be stored on the storage device 910 either before or after execution by the processor 704.

The devices and/or systems described in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document.

Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described above. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations that may be provided within at least one non-transitory, tangible, computer readable medium for execution by the one or more processors. An economy is achieved in that a flowchart as in FIG. 6 is used to describe both programs, and also methods. So, while flowcharts described methods in terms of boxes, they also concurrently describe programs.

Other implementations include combinations and sub-combinations of features described or shown in the drawings herein, including for example, implementations that are equivalent to: providing or applying a feature in a different order than in a described implementation, extracting an individual feature from one and inserting such feature into another implementations; removing one or more features from an implementation; or both removing one or more features from an implementation and adding one or more features extracted from one or more other implementations, while providing the advantages of the features incorporated in such combinations and sub-combinations. As used in this paragraph, feature or features can refer to the structures and/or functions of an apparatus, article of manufacture or system, and/or the steps, acts, or modalities of a method.

We claim:

1. A medical system for generating a data presentation for treatment of at least one health event of a patient, the medical system comprising:
 a wearable medical monitoring device comprising:
  one or more sensors to acquire data associated with the at least one health event including a cardiac anomaly;
  one or more treatment components for providing treatment of the cardiac anomaly; and
  one or more hardware processors and logic encoded in one or more non-transitory media for execution by the one or more hardware processors and when executed operable for:
   identifying the cardiac anomaly indicated by a particular portion of the data that meets a predefined magnitude, shape, and/or pattern during a time threshold indicative of the cardiac anomaly;
   specifying for independent recordings, data blocks of the data that characterize respective health episodes associated with the at least one health event including the particular portion of the data, wherein at least two of the data blocks are independently recorded in response to different trigger sources; and
   separately storing the data blocks;
 at least one data management device configured for:
  determining one or more relationships of the data blocks;

stitching the data blocks along a timeline for storage in a record as a full episode according to the one or more relationships; and providing the record including the stitched data blocks to a display;

the display configured for:

receiving the stitched data blocks; and rendering on a visual user interface of the display, a data presentation showing the timeline and graphic representations of the stitched data blocks along the timeline thereby displaying the full episode of the at least one health event by depicting the one or more relationships of the data blocks to determine a treatment protocol for the cardiac anomaly, wherein the one or more treatment components of the wearable medical monitoring device are configured to provide the treatment in response to the treatment protocol.

2. The medical system of claim 1, wherein specifying the respective data blocks for independent recording includes opening a recording of a particular episode of the respective health episodes at a first time and a closing the recording of the particular episode at a subsequent second time.

3. The medical system of claim 2, wherein the opening of the particular episode is, at least in part, in response to the wearable medical monitoring device determining at least a first portion of the data meets initiation criteria associated with the at least one health event, and the closing of the particular episode is, at least in part, in response to the wearable medical monitoring device determining at least a second portion of the data meets an end criteria associated with the at least one health event.

4. The medical system of claim 2, wherein the wearable medical monitoring device is configured for wear by the patient and further comprises a user input interface to receive a user trigger, and wherein the opening of the particular episode and/or the closing of the particular episode is, at least in part, in response to the wearable medical monitoring device receiving the user trigger.

5. The medical system of claim 2, wherein the at least one data management device includes an assistant device positioned local to the patient, the assistant device comprising:

an interface to request from the wearable medical monitoring device, the data up to a current point in time to define the subsequent second time for closing the particular episode;

a receiver to receive the data blocks from the wearable medical monitoring device; and a transmitter to transfer the data blocks to a remote data management module for stitching the data blocks and providing the data presentation.

6. The medical system of claim 5, wherein the assistant device receives supplemental information from the patient and the supplemental information is transferred to the data management module for integration in the data presentation.

7. The medical system of claim 1, wherein the at least one health event includes a first health event and a second health event, and wherein at least a first particular data block is specified that characterizes a first health episode of the respective health episodes associated with the first health event and a second particular data block is specified that characterizes a second health episode of the respective health episodes associated with the second health event.

8. The medical system of claim 1, wherein the data blocks are transmitted collectively in a data group to the at least one data management device.

9. The medical system of claim 8, wherein the relationship includes a first data block of a first episode is a parent and a second data block of a second episode is a child, in which recording of the first episode is already open and recording of the second episode is opened while the first episode is still recording, and wherein the operations further including:

pausing the transmitting of first data block and the second data block as the data group until recording of first data block and the second data block is complete.

10. The medical system of claim 1, wherein the data blocks include at least two data blocks having at least a portion of overlapping data in a segment of time.

11. The medical system of claim 1, wherein the wearable medical monitoring device includes a first data source to acquire a first data type and a second data source to acquire a second data type, and wherein graphical representations of the stitched data blocks of the first data type and graphical representations of the stitched data blocks of the second data type are displayed along the timeline.

12. The medical system of claim 1, wherein the treatment protocol includes a shock treatment and the one or more treatment components are configured to administer the shock treatment.

13. The medical system of claim 12, wherein the health episodes includes a first shock treatment administered by the one or more treatment components, and a second shock treatment is provided by the one or more treatment components, according to the treatment protocol.

14. A method for a medical system generating a data presentation for treatment of at least one health event of a patient, the method comprising:

acquiring, by one or more sensors of a wearable medical monitoring device of the medical system, data associated with the at least one health event including a cardiac anomaly;

identifying, by the wearable medical monitoring device, the cardiac anomaly indicated by a particular portion of the data that meets a predefined magnitude, shape, and/or pattern during a time threshold indicative of the cardiac anomaly;

specifying for independent recordings, data blocks of the data that characterize respective health episodes associated with the at least one health event including the particular portion of the data, wherein at least two of the data blocks are independently recorded in response to different trigger sources;

separately storing the data blocks;

determining one or more relationships of the data blocks;

stitching, by at least one data management device of the medical system, the data blocks along a timeline according to the one or more relationships;

storing the stitched data blocks in a record as a full episode;

providing the record including the stitched data blocks to a display;

receiving, by the display, the stitched data blocks;

rendering, by the display on a visual user interface, a data presentation showing the timeline and graphic representations of the stitched data blocks along the timeline thereby displaying the full episode of the at least one health event by depicting the one or more relationships of the data blocks to determine a treatment protocol for the cardiac anomaly; and providing, by the wearable medical monitoring device, the treatment in response to the treatment protocol.

15. The method of claim 14, wherein specifying the respective data blocks includes opening a recording of a particular episode of the respective health episodes at a first time and a closing the recording of the particular episode at a subsequent second time.

16. The method of claim 15, wherein opening the particular episode is, at least in part, in response to determining that at least a first portion of the data meets initiation criteria associated with the at least one health event, and closing the particular episode is, at least in part, in response determining that at least a second portion of the data meets an end criteria associated with the at least one health event.

17. The method of claim 15, further comprising:
receiving a user trigger, and
wherein opening the particular episode and/or closing the particular episode is, at least in part, in response to receiving the user trigger.

18. The method of claim 15, further comprising:
requesting from the wearable medical monitoring device, the data up to a current point in time to define the subsequent second time for closing the particular episode;
receiving the data blocks from the wearable medical monitoring device; and
transferring the data blocks to a remote data management module for stitching the data blocks and providing the data presentation.

19. A medical system for generating a data presentation for treatment of a cardiac anomaly event of a patient, the medical system comprising:
a wearable cardiac monitoring device comprising:
one or more electrode sensors to acquire electrocardiogram data associated with the cardiac anomaly event of the patient;
one or more treatment components for providing treatment of the cardiac anomaly; and
one or more hardware processors and logic encoded in one or more non-transitory media for execution by the one or more hardware processors and when executed operable for:
identifying the cardiac anomaly indicated by a particular portion of the data that meets a predefined magnitude, shape, and/or pattern during a time threshold indicative of the cardiac anomaly;
specifying for independent recordings, data blocks of the electrocardiogram data that characterize respective health episodes associated with the cardiac anomaly event, by opening an episode of the respective health episode at a first time and a closing the respective health episode at a second time, wherein at least two of the data blocks are independently recorded in response to different trigger sources; and
separately storing the data blocks; and
at least one data management device configured for:
determining one or more relationships of the data blocks;
stitching the data blocks along a timeline for storage in a record as a full episode according to the one or more relationships; and
storing the stitched data blocks in a record as a full episode; and
providing the record including the stitched data blocks to a display;
the display configured for:
receiving the stitched data blocks; and
rendering on a visual user interface of the display, a data presentation showing the timeline and graphic representations of the stitched data blocks along the timeline thereby displaying the full episode of the cardiac anomaly by depicting the one or more relationships of the data blocks to determine a treatment protocol for the cardiac anomaly,
wherein the one or more treatment components of the wearable cardiac medical monitoring device are configured to provide the treatment in response to the treatment protocol.

20. The medical system of claim 19, wherein the wearable cardiac monitoring device further includes a defibrillator for providing treatment of the cardiac anomaly.

21. The medical system of claim 19, wherein the at least one data management device includes a mobile assistant device positioned local to the patient, the mobile assistant device comprising:
an interface to request from the wearable cardiac monitoring device, the electrocardiogram data up to a current point in time to define the second time for closing the episode;
a user input interface to receive symptomatic supplemental information from the patient;
a receiver to receive the data blocks from the wearable cardiac monitoring device; and
a transmitter to transfer the data blocks and supplemental information to a remote data management module for stitching the data blocks and providing the data presentation.

* * * * *